(12) United States Patent
Mitchell et al.

(10) Patent No.: US 9,085,830 B2
(45) Date of Patent: Jul. 21, 2015

(54) APPARATUS FOR CONTROLLED ELECTROSPINNING

(75) Inventors: Stuart B. Mitchell, Lake Forest Park, WA (US); Joan E. Sanders, Sammamish, WA (US)

(73) Assignee: University of Washington, Seattle, WA (US)

( * ) Notice: Subject to any disclaimer, the term of this patent is extended or adjusted under 35 U.S.C. 154(b) by 1050 days.

(21) Appl. No.: 13/176,501

(22) Filed: Jul. 5, 2011

(65) Prior Publication Data

US 2012/0009292 A1      Jan. 12, 2012

Related U.S. Application Data

(62) Division of application No. 11/609,774, filed on Dec. 12, 2006, now Pat. No. 7,981,353.

(60) Provisional application No. 60/749,450, filed on Dec. 12, 2005.

(51) Int. Cl.
*D01D 5/00* (2006.01)
*A61L 27/14* (2006.01)
*A61L 27/18* (2006.01)
*B29C 47/92* (2006.01)

(52) U.S. Cl.
CPC ............. *D01D 5/0076* (2013.01); *A61L 27/14* (2013.01); *A61L 27/18* (2013.01); *B29C 47/92* (2013.01); *D01D 5/0092* (2013.01)

(58) Field of Classification Search
CPC ..... D01D 5/0076; D01D 5/0092; B29C 47/92
USPC ..................... 425/144, 145, 174.8 E
See application file for complete search history.

(56) References Cited

U.S. PATENT DOCUMENTS

| | | | |
|---|---|---|---|
| 2,160,962 A | * | 6/1939 | Formhals .................. 264/10 |
| 4,689,186 A | | 8/1987 | Bornat |
| 2002/0089094 A1 | | 7/2002 | Kleinmeyer |
| 2002/0090725 A1 | | 7/2002 | Simpson |

(Continued)

OTHER PUBLICATIONS

Annis, D., et al., "An Elastomeric Vascular Prosthesis," Transactions—American Society for Artificial Internal Organs 24:209-214, 1978.

(Continued)

*Primary Examiner* — Yogendra Gupta
*Assistant Examiner* — Joseph Leyson
(74) *Attorney, Agent, or Firm* — Christensen O'Connor Johnson Kindness PLC

(57) ABSTRACT

An electrospinning apparatus and methodology is described that produces medical devices, such as scaffolds that induce the formation of a natural fibrous structure (primarily collagen and elastin) in a tissue-engineered medical device. The apparatus uses collection surfaces designed to manipulate or change the electrostatic field so that the electrospun fibers are arranged in desirable patterns that are similar to or mimic the fibrillar structure of an animal tissue. The manipulation results in fibers that are preferentially oriented in a predefined pattern. In addition, the interfiber space between the fibers and the fiber diameter are consistently within a predefined range. Using these techniques in conjunction with controlling polymer properties enables the production of a scaffold that has the structural and mechanical characteristics similar to the native tissue.

26 Claims, 12 Drawing Sheets

(56) References Cited

U.S. PATENT DOCUMENTS

| | | | |
|---|---|---|---|
| 2002/0175449 A1* | 11/2002 | Chu et al. | 264/465 |
| 2006/0135020 A1 | 6/2006 | Weinberg | |
| 2008/0122142 A1 | 5/2008 | Kim | |

OTHER PUBLICATIONS

Bognitzki, M., et al., "Nanostructured Fibers via Electrospinning," Advanced Materials 13(1):70-72, 2001.

Boland, E.D., et al., "Tailoring Tissue Engineering Scaffolds Using Electrostatic Processing Techniques: a Study of Poly(Glycolic Acid) Electrospinning," Journal of Macromolecular Science: Pure and Applied Chemistry 38A(12):1231-1243, 2001.

Brauker, J.H., et al., "Neovascularization of Synthetic Membranes Directed by Membrane Microarchitecture," Journal of Biomedical Materials Research 29(12):1517-1524, 1995.

Buer, A., et al., "Electrospinning and Properties of Some Nanofibers," Textile Research Journal 71(4):323-328, 2001.

Deitzel, J.M., et al., "Controlled Deposition of Electrospun Poly(Ethylene Oxide) Fibers," Polymer 42(19):8163-8170, 2001.

Deitzel, J.M., et al., "The Effect of Processing Variables on the Morphology of Electrospun Nanofibers and Textiles," Polymer 42(1):261-272, 2001.

Demir, M.M., et al., "Electrospinning of Polyurethane Fibers," Polymer 43(11):3303-3309, 2002.

Doshi, J., and D.H. Reneker, "Electrospinning Process and Applications of Electrospun Fibers," Journal of Electrostatics 35(1-2):151-160, 1995.

Fong, H., et al., "Beaded Nanofibers Formed During Electrospinning," Polymer 40(16):4585-4592, 1999.

Fridrikh, S.V., et al., "Controlling the Fiber Diameter During Electrospinning," Physical Review Letters 90(14):144502-1-114502-4, 2003.

Gibson, P.W., et al., "Electrospun Fiber Mats: Transport Properties," AIChE (American Institute of Chemical Engineers) Journal 45(1):190-195, Jan. 1999.

Hohman, M.M., et al., "Electrospinning and Electrically Forced Jets. I. Stability Theory," Physics of Fluids 13(8):2201-2220, Aug. 2001.

Hohman, M.M., et al., "Electrospinning and Electrically Forced Jets. II. Applications," Physics of Fluids 13(8):2221-2236, Aug. 2001.

Huang, L., et al., "Engineered Collagen—PEO Nanofibers and Fabrics," Journal of Biomaterial Science: Polymer Edition 12(9):979-993, 2001.

Jin, H.-J., et al., "Electrospinning Bombyx mori Silk With Poly(Ethylene Oxide)," Biomacromolecules 3(16):1233-1239, 2002.

Larrondo, L., and R.S.J. Manley, "Electrostatic Fiber Spinning From Polymer Melts I. Experimental Observations on Fiber Formation and Properties," Journal of Polymer Science: Polymer Physics Edition 19(6):909-920, 1981.

Larrondo, L., and R.S.J. Manley, "Electrostatic Fiber Spinning From Polymer Melts II. Examination of the Flow Field in an Electrically Driven Jet," Journal of Polymer Science: Polymer Physics Edition 19(6):921-932, 1981.

Larrondo, L., and R.S.J. Manley, "Electrostatic Fiber Spinning From Polymer Melts III. Electrostatic Deformation of a Pendant Drop of Polymer Melt," Journal of Polymer Science: Polymer Physics Edition 19(6):933-940, 1981.

Lee, K.H., et al., "Characterization of Nano-Structured Poly(ε-Caprolactone) Nonwoven Mats via Electrospinning," Polymer 44(4):1287-1294, 2003.

Li, W.-J., et al., "Electrospun Nanofibrous Structure: a Novel Scaffold for Tissue Engineering," Journal of Biomedical Materials Research 60(4):613-621, 2002.

Liu, H., and Y.-L. Hsieh, "Ultrafine Fibrous Cellulose Membranes From Electrospinning of Cellulose Acetate," Journal of Polymer Science, Part B: Polymer Physics 40(18):2119-2129, 2002.

Matsuda, T., and Y. Nakayama, "Surface Microarchitectural Design in Biomedical Applications: in Vitro Transmural Endothelialization on Microporous Segmented Polyurethane Films Fabricated Using an Excimer Laser," Journal of Biomedical Materials Research 31:235-242, 1996.

Matthews, J.A., et al., "Electrospinning of Collagen Nanofibers," Biomacromolecules 3:232-238, 2002.

Mitchell, S.B., "Electrospinning Controlled Architecture Scaffolds for Tissue Engineering and the Effect of Scaffold Mechanical Properties on Collagen Synthesis in Tissue Engineered Mitral Valves," Doctoral Dissertation, University of Washington, Seattle, 2004.

Mo, X.M., et al., "Electrospun P(LLA-CL) Nanofiber: a Biomimetic Extracellular Matrix for Smooth Muscle Cell and Endothelial Cell Proliferation," Biomaterials 25(10):1883-1890, 2004.

Nakayama, Y., et al., "Surface Microarchitectural Design in Biomedical Applications: in Vivo Analysis of Tissue Ingrowth in Excimer Laser-Directed Micropored Scaffold for Cardiovascular Tissue Engineering," Journal of Biomedical Materials Research 51(3):520-528, 2000.

Norris, I.D., et al., "Electrostatic Fabrication of Ultrafine Conducting Fibers: Polyaniline/Polyethylene Oxide Blends," Synthetic Metals 114:109-114, 2000.

Sanders, J.E., et al., "Tissue Response to Single-Polymer Fibers of Varying Diameters: Evaluation of Fibrous Encapsulation and Macrophage Density," Journal of Biomedical Materials Research 52(1):231-237, 2000.

Shin, Y.M., et al., "Electrospinning: a Whipping Fluid Jet Generates Submicron Polymer Fibers," Applied Physics Letters 78(8):1149-1151, 2001.

Shin, Y.M., et al., "Experimental Characterization of Electrospinning: the Electrically Forced Jet and Instabilities," Polymer 42(25):9955-9967, 2001.

Spivak, A.F., et al., "A Model of Steady State Jet in the Electrospinning Process," Mechanics Research Communications 27(1):37-42, 2000.

Spivak, A.F., and Y.A. Dzenis, "Asymptotic Decay of Radius of a Weakly Conductive Viscous Jet in an External Electric Fluid," Applied Physics Letters 73(21):3067-3069, 1998.

Srinivasan, G., and D.H. Reneker, "Structure and Morphology of Small Diameter Electrospun Aramid Fibers," Polymer International 36(2):195-201, 1995.

Theron, A., et al., "Electrostatic Field-Assisted Alignment of Electrospun Nanofibers," Nanotechnology 12(3):384-390, 2001.

Theron, S.A., et al., "Experimental Investigation of the Governing Parameters in the Electrospinning of Polymer Solutions," Polymer 45(6):2017-2030, 2004.

Wilson, G.J., et al., "A Compliant Corethane/Dacron Composite Vascular Prosthesis: Comparison With 4-mm ePTFE Grafts in a Canine Model," ASAIO (American Society for Artificial Internal Organs) Journal 39(3):M52-531, 1993.

Yarin, A.L., et al., "Bending Instability in Electrospinning of Nanofibers," Journal of Applied Physics 89(5):3018-3026, 2001.

Yarin, A.L., et al., "Taylor Cone and Jetting From Liquid Droplets in Electrospinning of Nanofibers," Journal of Applied Physics 90(9):4836-4846, 2001.

Zong, X., et al., "Structure and Process Relationship of Electrospun Bioabsorbable Nanofiber Membranes," Polymer 43(16):4403-4412, 2002.

* cited by examiner

APPARATUS FOR CONTROLLED ELECTROSPINNING

CROSS-REFERENCES TO RELATED APPLICATIONS

This application is a division of U.S. patent application Ser. No. 11/609,774, filed Dec. 12, 2006, now U.S. Pat. No. 7,981,353, which claims the benefit of U.S. Provisional Application No. 60/749,450, filed Dec. 12, 2005, both of which applications are incorporated herein in their entirety by reference.

STATEMENT OF GOVERNMENT LICENSE RIGHTS

This invention was made with government support under grant number EEC9529161 awarded by the National Science Foundation. The government has certain rights in the invention.

BACKGROUND

Valvular heart disease has a mortality rate of approximately 40% in the United States alone. The major reason for this high mortality is the lack of a suitable replacement for diseased valves. Current replacement valves lack either the structural, functional (mechanical), or both structural and functional characteristics of the native valves they are intended to replace. These deficiencies result in the manifestation of a variety of valve rejection and failure problems.

The engineering of substitute heart valves using biodegradable scaffolds and autologous cells has undergone considerable advances in recent years. Research conducted attempting to optimize cell source and culturing techniques for developing functional tissues has had promising results. However, in vivo studies resulted in valves that did not perform as well as the native valves they were intended to replace. Accordingly, there continues to be a need for artificial implantable medical devices, such as heart valves.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In view of the foregoing, an embodiment of the invention is a medical device having either or both the structural and mechanical characteristics of the native tissue that the medical device is intended to replace or mimic. Embodiments of the medical device can be made from biological proteins, synthetic polymers, natural fibers, non-synthetic polymers, and combinations of any of these in conjunction with autologous cells to engineer a tissue that will mimic the structural, mechanical, or functional characteristics of the native tissue. As an alternative to autologous cells, various different cell types/lines could be used, including stem cells and progenitor cells.

In another embodiment of the invention, an electrospinning apparatus and methodology is described that produces medical devices, such as scaffolds that induce the formation of a natural fibrous structure (primarily collagen and elastin) in the tissue-engineered medical device. In addition, the formation of the appropriate structure results in mechanical properties of the tissue-engineered medical device that are similar to the mechanical properties of normal native tissue.

The apparatus uses collection surfaces designed to manipulate or change the electrostatic field so that the electrospun fibers are arranged in desirable patterns that are similar to or mimic the fibrillar structure of an animal tissue. The manipulation results in fibers that are preferentially oriented in a predefined pattern. In addition, the interfiber space between the fibers and the fiber diameter are consistently within a predefined range. Using these techniques in conjunction with controlling polymer properties enables the production of a scaffold that has the structural and mechanical characteristics similar to the native tissue.

The scaffolds may be seeded with autologous cells after which the cells begin to produce extracellular matrix proteins (collagen, elastin, glycosaminoglycans). The scaffold with known mechanical properties and fiber architectures control collagen synthesis through cellular interaction with the scaffold. The scaffold mechanical properties that influence extracellular matrix formation are the stress-strain relationship, stiffness, and polymer degradation rate. The result, when the architecture and mechanical properties are controlled correctly, is a functional tissue-engineered valve with properties similar to the native valve.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
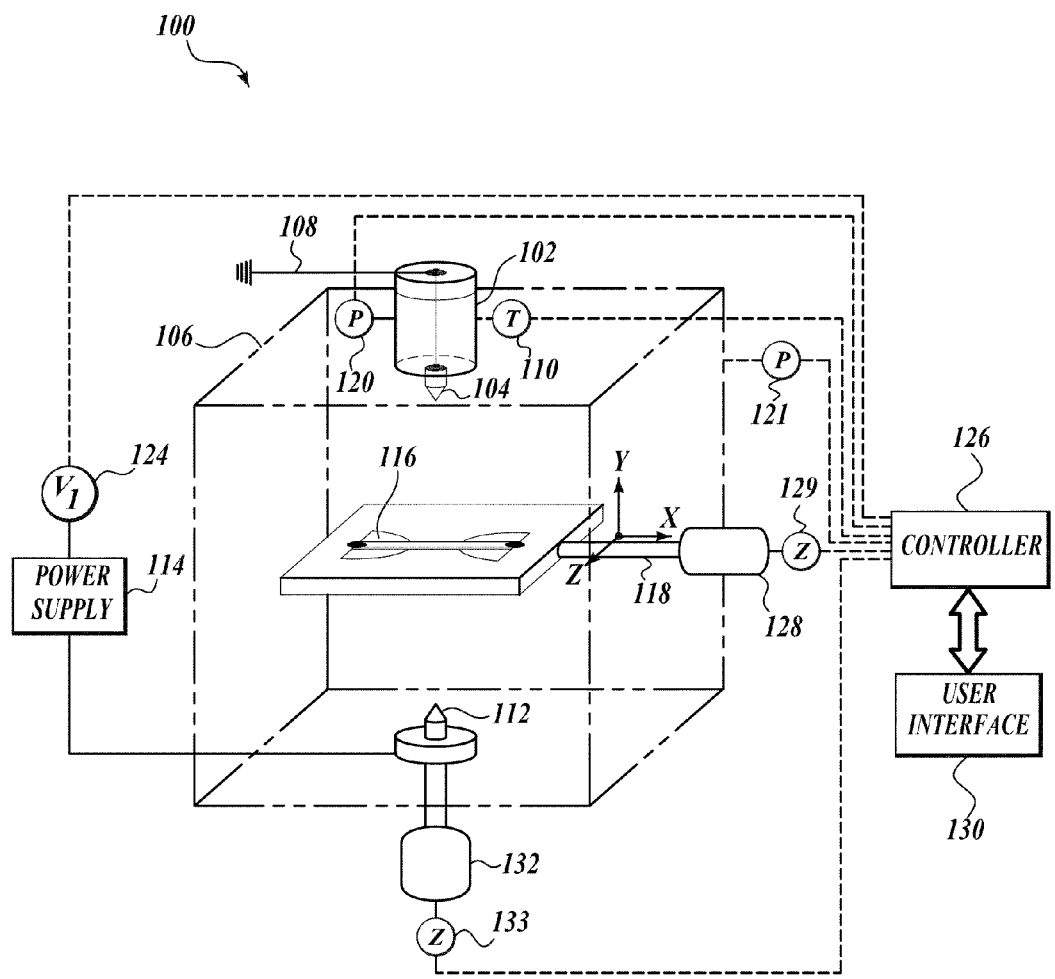
FIG. 1 is a diagrammatical illustration of an electrospinning apparatus in accordance with one embodiment of the present invention.

FIG. 1 is a diagrammatical illustration of an electrospinning apparatus 100 in accordance with one embodiment of the invention. The electrospinning apparatus 100 includes a reservoir 102 or chamber for containing a spinning dope. The spinning dope may be a polymer solution, a polymer melt, or any material capable of being spun. A polymer that may be used is a polyurethane, and specifically a degradable polyurethane, such as an amino acid-based polyurethane. The reservoir 102 is a container that may be sealed in a pressure-tight manner. The reservoir 102 includes a nozzle 104 at the bottom of the reservoir 102 through which the spinning dope is extruded and/or drawn by an electrostatic force, as will be described in greater detail below. The dope may be subjected to pressure and/or a vacuum via a plunger or via a means for applying pressure within the reservoir 102 that delivers the dope to the nozzle 104. For example, pressurized air or vacuum may be supplied to the reservoir 102 by dedicated lines having control valves that are under the control of a controller.

The apparatus 100 may include an enclosure 106. In one embodiment, the enclosure 106 includes a six-sided vessel. The enclosure 106 may include one or more ports for delivering a pressurized gas to the interior of the enclosure 106. The gas may be nitrogen, for example. Alternatively, a vacuum may be applied to the enclosure 106. Pressurized gas lines and vacuum lines may include automated valves connected to a controller to control the pressure and/or vacuum within the enclosure 106. In one embodiment, the reservoir 102 is placed on the upper wall of the enclosure 106 so that the nozzle 104 projects downward into the enclosure 106.

The nozzle 104 is connected to a first electrode 108. The electrode 108 is grounded or at least a potential lower than a second electrode described below. For purposes of controlling the spinning dope viscosity, a temperature sensor 110 may be positioned at the reservoir 102 to measure the temperature of the reservoir 102 and/or the dope inside of the reservoir 102. Heating coils (not shown) may be wrapped around the exterior of the reservoir 102 to maintain the reservoir and/or the dope at a predetermined temperature. Heating may be provided by electrical heat tracing or tubing provided with a heating medium, such as a hot fluid or steam.

Figure 16:
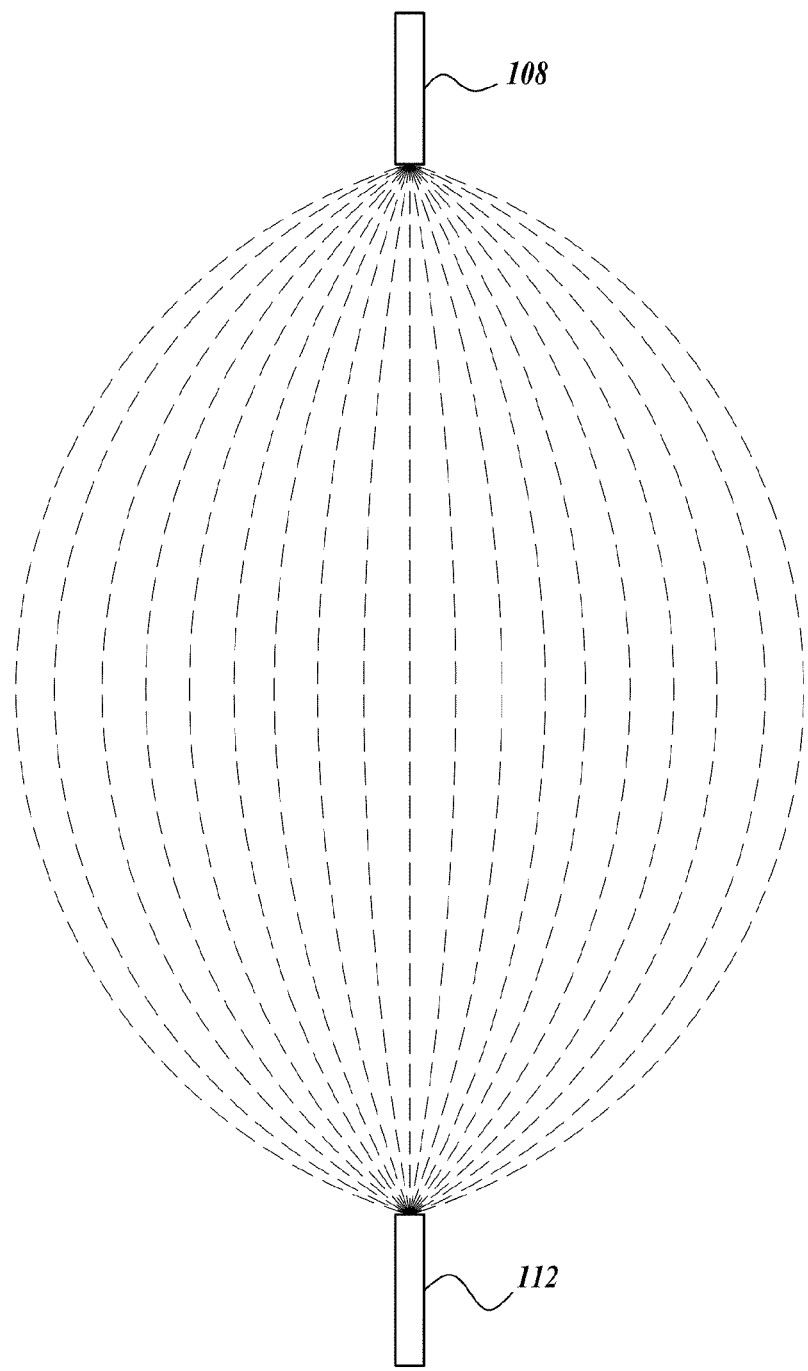
FIG. 16 is a diagrammati
cal illustration of an undisturbed electrostatic field generated between a first electrode and second electrode.
Figure 17:
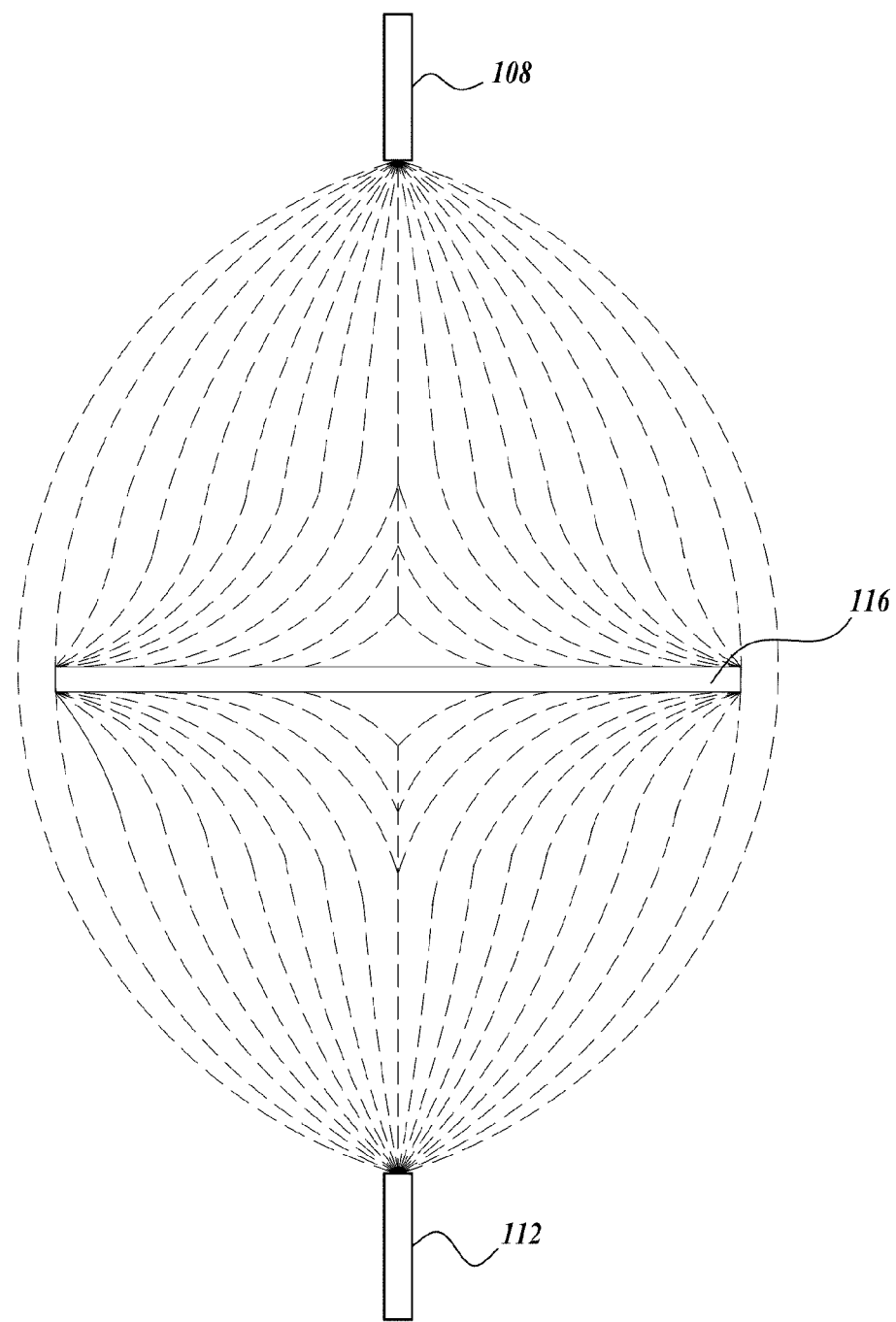
FIG. 17 is a diagrammatical illustration of an electrostatic field interfered with or manipulated by a collection surface in accordance with the invention.

The second electrode 112 is positioned opposite to the first electrode 108 and at a distance removed from the first electrode 108 at the bottom wall of the enclosure 106 facing upward. In one embodiment, the second electrode 112 is connected to a high voltage power supply 114 that applies a high voltage to the second electrode 112. When the first electrode 108 is at a potential lower than the second electrode 112, an electrostatic field is created between the first 108 and the second 112 electrodes, having generally undisturbed parallel lines of electrostatic force (field lines) as illustrated in FIG. 16. In one aspect of the invention, the electrostatic field between the first 108 and the second 112 electrodes is interfered with, manipulated, or caused to be changed so that desired patterns are created in the electrostatic field lines of force, either by interference with or by the creation of a second electrostatic field, so that the fibers spun via the electrospinning apparatus 100 lie according to the patterns created by the interference with, the changes, or the second electrostatic field. For example, in FIG. 17, the lines of force of the electrostatic field have been changed by placing a collection surface 116 between the first electrode 108 and the second electrode 112.

In the technique of electrospinning, an electrostatic force is used to draw fine jets of dope from the reservoir. Dope held by surface tension at the nozzle is subjected to an electrostatic field that induces a charge at the surface. Mutual charge repulsion causes a force directed opposite to the surface tension. When the electrostatic field intensity is sufficiently strong, forces on the surface of the dope at the tip of the nozzle overcome the surface tension, the surface elongates, and makes a fine jet in the direction of the applied field (perpendicular to the liquid surface). As the jet travels towards the electrode of the applied voltage, the dope is collected as a non-woven mesh of fine fibers. The conventional electrospinning apparatus has a plate, screen, or a rotating mandrel positioned beneath the nozzle that is connected to the bottom electrode. Therefore, the pattern of fibers that is produced is in accordance with an undisturbed electrostatic field.

Figures 3, 4:
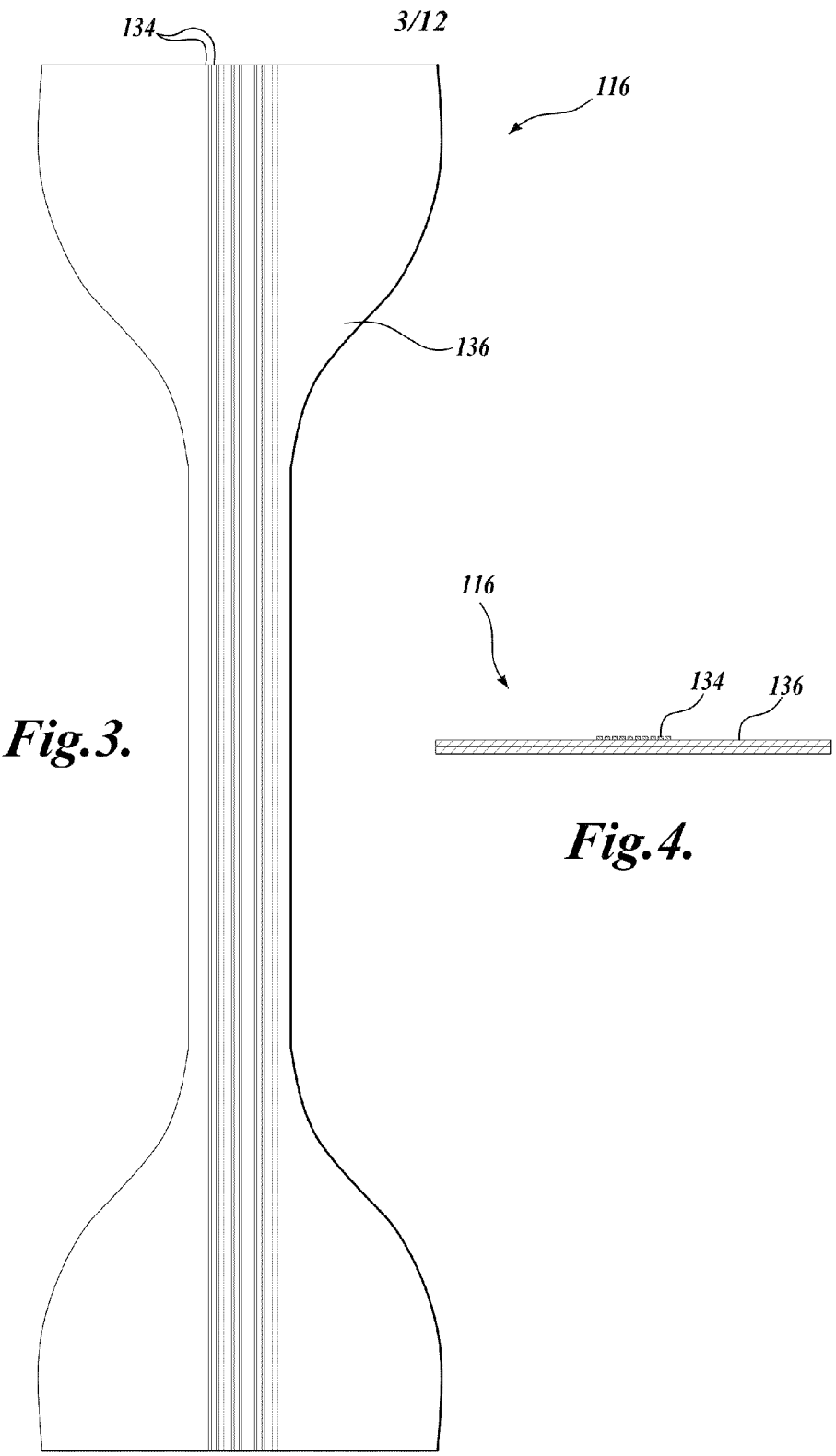
FIG. 3 is a diagrammatical illustration of a collection surface in accordance with one embodiment of the present invention.
FIG. 4 is a diagrammatical illustration of a cross section of a collection surface in accordance with one embodiment of the present invention.

In one embodiment of the invention, the electrostatic field created between the first electrode 108 and the second electrode 112 is interfered with, manipulated, or changed to have a desirable pattern by a collection surface 116 that is interposed between the first 108 and the second 112 electrodes, so that the collection surface 116 is isolated from the first 108 and the second 112 electrodes. The collection surface 116 may be electrically isolated from the first 108 and the second 112 electrodes. This configuration avoids influencing the collection surface 116 either through the ground or charged electrode. This configuration further enables exploration of the influence of the collection surface characteristics on mesh architecture and fiber morphology. The collection surface 116 can be made from a dielectric material, a conductive material, or any combination of both a dielectric material and a conductive material. The collection surface 116 interferes with, and causes a change or disturbance in the electrostatic field, such as illustrated in FIG. 1. The resulting non-woven mesh has fibers that are random. In other embodiments as is illustrated in FIGS. 3 and 4, the collection surface 116 may have parallel conductive wires 134, wherein the conductive wires 134 causes alignment of the fibers parallel to the conductive wires 134, resulting in non-woven meshes having an array of non-random fibers corresponding to each conductive wire 134. A dielectric material 136 is exposed between and separates the conductive wires 134, so that random fibers are deposited between non-random fibers, resulting in a non-woven mesh having arrays of non-random fibers and random fibers between arrays that attach adjacent arrays to one another. It is to be appreciated that the collection surface 116 illustrated in FIGS. 3 and 4 is a representative collection surface 116. Other embodiments of the collection surface 116 can have conductive wires arranged in different patterns. Furthermore, the collection surface 116 can be made entirely from dielectric materials, entirely from conductive materials, or any combination of dielectric materials and conductive materials. Additionally, conductive materials can be layered alternately with dielectric materials to create arrays of non-random fibers connected by random fibers. Each configuration of the collection surface 116 results in influencing the lines of force in the electrostatic field created between the first 108 electrode and the second 112 electrode. By placing conductive materials appropriately on the collection surface 116, the alignment of the electro spun fibers can be made to align in patterns that mimic the fibrillar structure of native tissue that the meshes are intended to replace. As an alternative to a planar collection surface, such as the illustrated collection surface 116, the collection surface can be disposed on a rotating mandrel, for example, a cylindrical mandrel, positioned between the first electrode 108 and the second electrode 112 with the longitudinal axis along the "X" axis. In this latter embodiment, the rotating mandrel collects fibers to form scaffold tubes. Further, this embodiment may be used in the embodiment of the apparatus 100 illustrated in FIG. 1 in place of the collection surface 116. The mandrel can be made from dielectric materials, conductive materials, or both types of materials.

Returning to FIG. 1, a translation stage 118 is connected to the collection surface 116 to translate the collection surface 116 in three (3) dimensions. The translation stage 118 includes an actuator 128 that moves the translation arm vertically or in any position parallel to a horizontal plane. The translation stage 118 may be connected to linear actuators for moving the translation stage in the X, Y, and Z directions. The translation stage 118 is controlled to move in the horizontal plane so that the electrospun fibers cover the desired portions of the collection surface 116. The translation stage 118 includes a position indicating transmitter 129 to determine and control the position of the collection surface 116 via a controller.

The apparatus 100 may include instrumentation to control process variables and parameters. For example, a pressure transmitter 120 monitoring the pressure and/or vacuum inside the reservoir 102 may be used to control the pressure and/or vacuum inside of the reservoir 102 to provide a steady supply of dope to the nozzle 104 at a generally constant mass flow rate. Additionally, a temperature transmitter 110 to measure the temperature of the reservoir 102 and/or the dope inside the reservoir 102 may be provided to control the temperature of the spinning dope. A measurement of the temperature of the dope is an indirect way of obtaining the viscosity of the dope. Translation stage 118 position is measured by position indicating transmitter 129, and consequently collection surface 116 distance from the nozzle 104, is controlled by one or more actuators 128 that can move the collection surface 116 toward and away from the nozzle 104. Additionally, the second electrode 112 can be attached to an actuator 132 so as to vary the distance between the first electrode 108 and the second electrode 112. Toward this end, a position indicating transmitter 133 is located at the actuator 132 to measure and control the position of the second electrode 112 and so, control the distance between the first electrode 108 and the second electrode 112. A voltage transmitter 124 is provided at the power supply 114 to measure and control the voltage at the second electrode 112. The enclosure 106 may include a pressure/vacuum transmitter 121 to measure and control pressure and/or vacuum within the enclosure 106 via the operation of an automated valve, for example. To vary the dielectric strength of the collection surface 116, different dielectric materials, such as polystyrene, Teflon™, and Pyrex™ can be used for the collection surface 116. The various instruments are connected to a controller 126. As is well known in the art, a controller 126 can have any number of signal conditioning modules so as to be able to read, convert, or digitize, and process the signals from the various instruments. The controller 126 includes a processor that can be provided with instructions to follow a particular algorithm to maintain the desired variable at a predetermined setpoint. The controller 126 is connected to a user interface 130 to allow a user to make adjustments to any one of the setpoints so as to move the desired measured or controlled variable to the setpoint.

While representative instrumentation has been described to control various parameters of the apparatus 100, the electrospinning apparatus 100 may be adjustable in other ways. For example, the collection surface 116 area size can be controlled by replacing the collection surfaces with others of various sizes or shapes. Further, the degree of influence of the collection surface 116 on the electrostatic field can be controlled by selecting various dielectric materials and conductive materials. Those variables that were found to induce the greatest change in the electrostatic field magnitude and direction include: (1) the distance between the first 108 and second 112 electrodes; (2) the distance from the nozzle 104 to the collection surface 116; (3) the collection surface 116 dielectric strength; and (4) the collection surface 116 area.

In one embodiment, the electrospinning apparatus allows closed-loop control of at least a number of variables including: (1) the distance between the first 108 and second 112 electrodes; (2) the distance from the nozzle 104 to the collection surface 116; (3) the applied voltage 124; (4) the pressure/vacuum of the enclosure 106; and (5) the temperature 110 of the dope. The collection surface 116 dielectric strength may be controlled by the selection of materials, including polystyrene, Teflon™, and Pyrex™ The collection surface 116 area may be controlled by replacement with different sizes or shapes of the collection surface. Consequently, because of the closed-loop control, the resulting fibers had fiber diameters that are substantially consistent with small variations. Furthermore, closed-loop control also leads to the spacing between the fibers (the "interfiber spacing") being substantially consistent with small variations.

Figure 5:
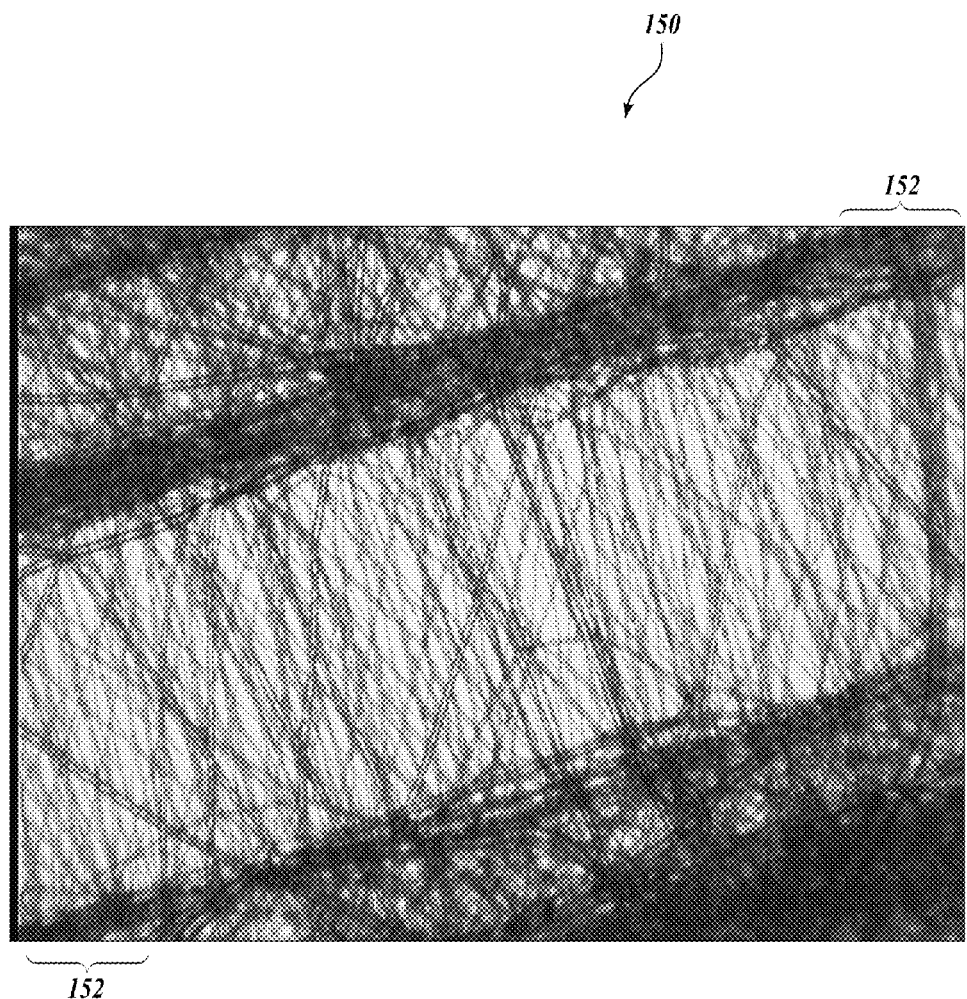
FIG. 5 is an image using light microscopy of fibers produced in accordance with one embodiment of the present invention.

FIG. 5 is an image using light microscopy of a non-woven mesh 150 produced using one embodiment of the apparatus 100. The collection surface used in making the non-woven mesh of FIG. 5 included alternating conductive copper wires disposed parallel to one another on a dielectric surface as shown in FIG. 3. The non-woven mesh 150 includes arrays 152 (the "dark" areas) of non-randomly oriented or arranged fibers (the "non-random" fibers) and randomly oriented or arranged fibers (the "random" fibers) between the arrays 152 that attach adjacent arrays 152 to each other. An array 152 is a collection of fibers or a zone of similarly oriented fibers in a non-woven mesh. The arrays 152 of non-random fibers have fibers that are generally aligned along a single direction and are generally parallel to one another, while the random fibers of the areas between arrays 152 are at varying angles to the direction of the generally parallel fibers of the arrays 152. The random fibers attach the adjacent arrays 152 to one another. The arrays 152 of non-random fibers are formed by alignment with the parallel conductive wires 134 of the collection surface 116. The random fibers are formed by the areas of dielectric surface 136 between the conductive wires 134.

Figure 6:
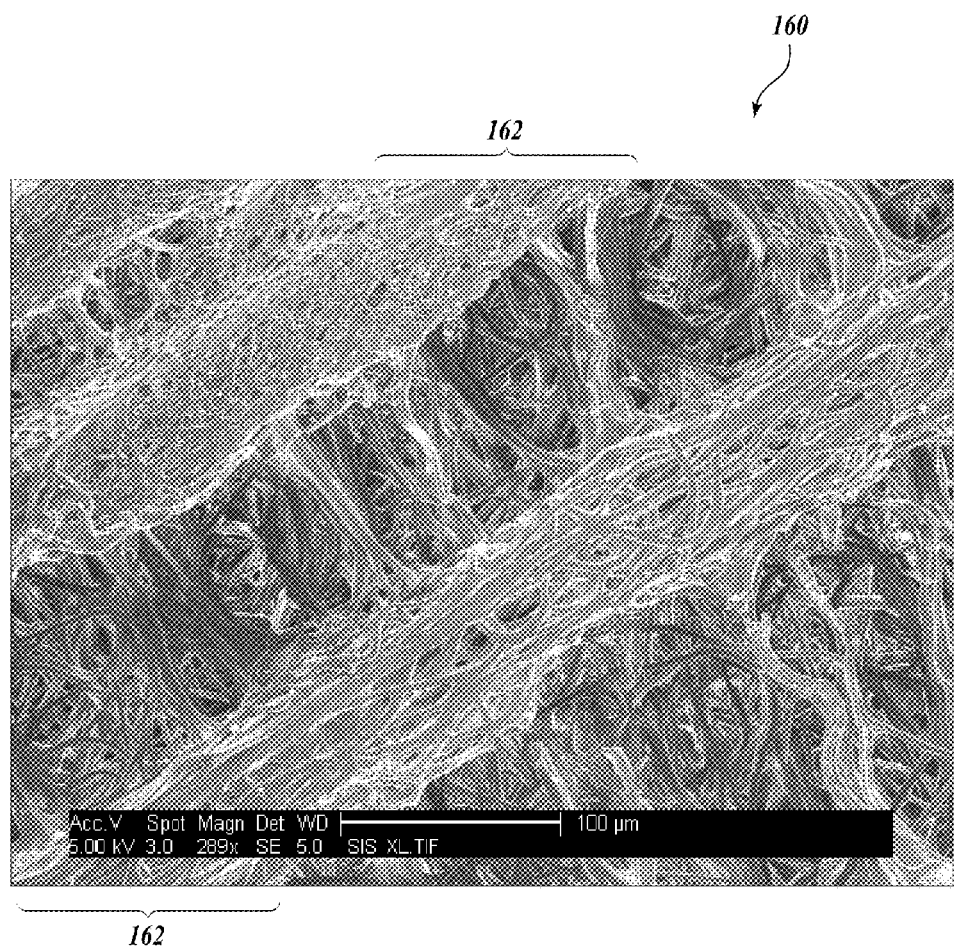
FIG. 6 is a scanning electron micrograph of fibers produced in accordance with one embodiment of the present invention.

FIG. 6 is a scanning electron micrograph of a non-woven mesh 160 produced using one embodiment of the apparatus of the invention. The collection surface used in making the non-woven mesh of FIG. 6 included alternating conductive copper wires disposed parallel to one another on a dielectric surface as shown in FIG. 3. The non-woven mesh 160 includes arrays 162 (the "light" areas) of non-randomly arranged fibers and randomly arranged fibers (the "dark" areas) between the arrays 162 that attach adjacent arrays 162 to each other. The arrays 162 of non-random fibers are generally aligned in a single direction and are generally parallel to one another, while the random fibers of the areas between arrays 162 are at varying angles to the generally parallel fibers of the arrays 162. The arrays 162 of non-random fibers are believed to be formed because the parallel conductive wires 134 of the collection surface 116 cause a realignment of the electrostatic field parallel to the conductive wires. In the areas where there are no conductive wires, random fibers are formed between the conductive wires 134. By varying the orientation of conductive wires 134, and by varying the distance between the wires on the collection surface, while providing dielectric materials between conductive wires 134, structured meshes having arrays of non-random fibers and random fibers can be produced.

Figure 7:
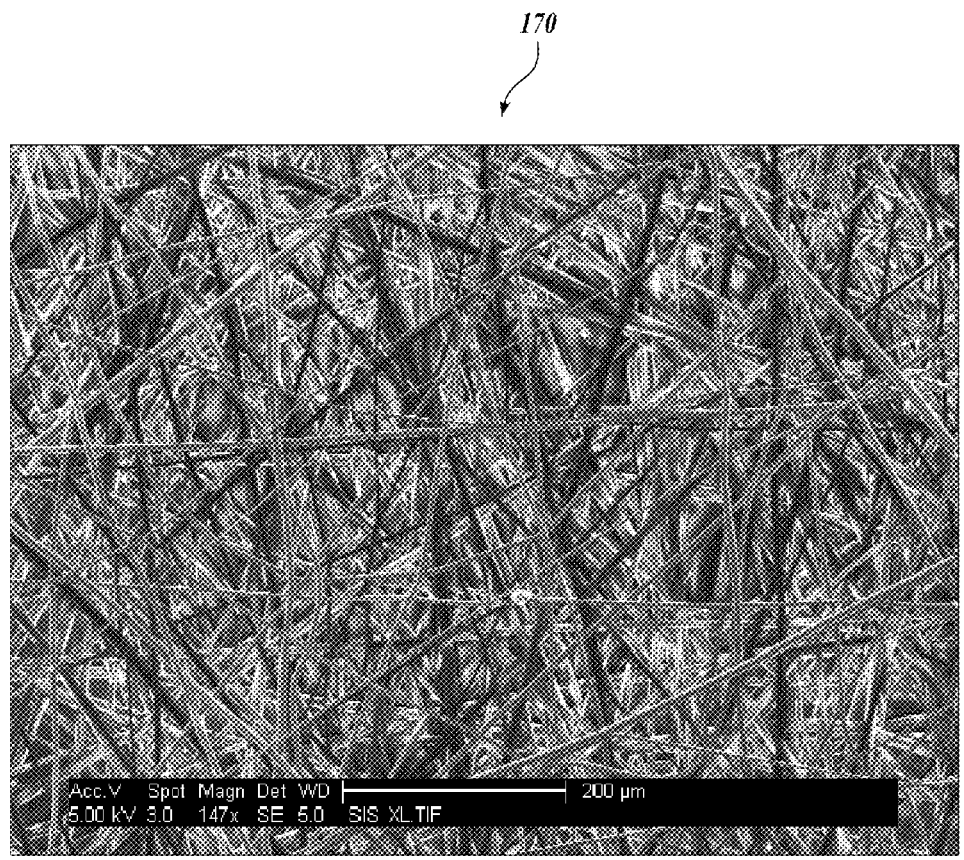
FIG. 7 is a scanning electron micrograph of fibers produced in accordance with one embodiment of the present invention.
Figure 8:
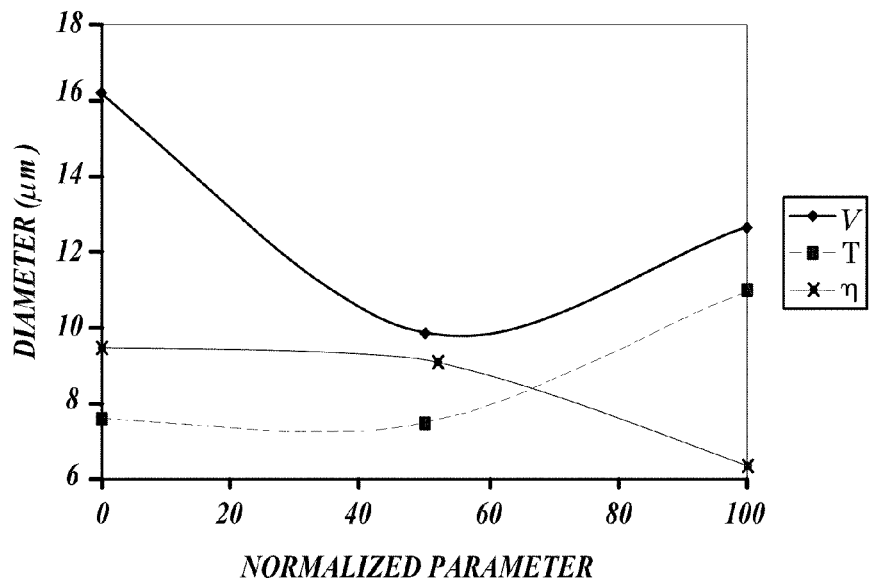
FIGS. 8 and 9 are graphs representing the fiber diameter dependence on voltage (V), temperature (T), ratio of collection surface distance from nozzle to distance between the electrodes ($\eta$), surface area (SA), dielectric strength (DS), and distance between the electrodes (De)
Figure 9:
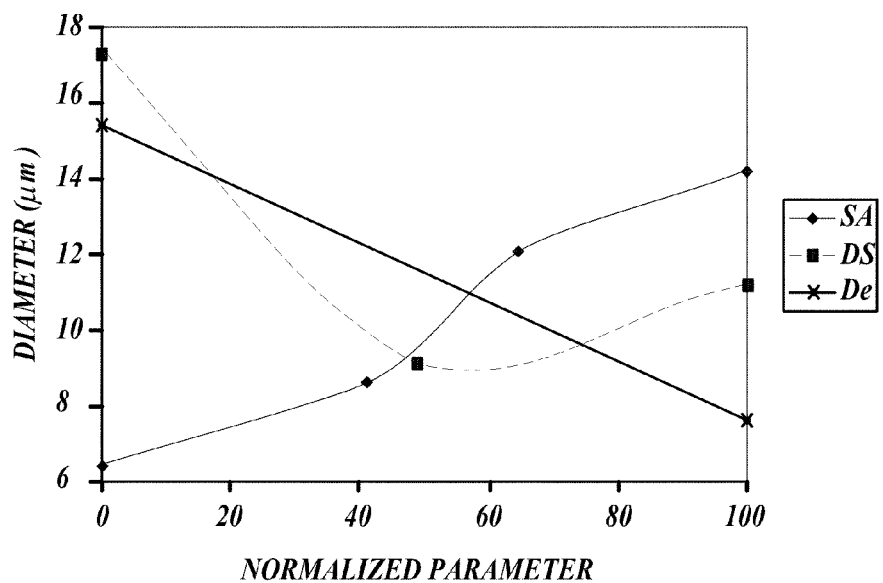

While FIGS. 5 and 6 depict representative non-woven meshes having non-random fibers and random fibers, the apparatus is not limited to producing such non-random fibers. FIG. 7 is a scanning electron micrograph of a non-woven mesh of random fibers. Because of the closed-loop control of one or more process parameters, the non-random fibers and the random fibers of the meshes produced have consistent fiber diameters and interfiber spacing heretofore not achieved by conventional electro spinning.

Morphological analysis of the fabricated non-woven meshes appear to suggest that the collection surface 116, including dielectric strength and surface area were found to be more significant than voltage and dope temperature at affecting fiber diameter and interfiber spacing. The collection surface 116, which was not connected to either electrode, substantially altered the electric field between the electrodes. Using the closed-loop controlled electrospinning apparatus 100, meshes with fiber diameters ranging from about 5 μm to about 18 μm with a variability less than about 1.8% were made. Interfiber spacing ranged from about 4 μm to about 90 μm with a variability less than about 20.2%. There was no significant difference for fiber diameter ($p=0.39$) over the range of about 8.6 μm to about 14.1 μm or for interfiber spacing ($p=0.20$) over the range of about 44.7 μm to about 82.9 μm. Fiber diameter and interfiber spacing were determined using the procedure set forth in Example 1 below in the section on Mesh Analysis. In determining the fiber diameter, an ellipse was fit to each fiber cross-section, and the minor axis length was determined. The minor axis length was considered to be the fiber diameter. An average interfiber spacing was determined using the stereological relationship for the mean free distance between particles in a two dimensional plane. The interfiber spacing was defined as the edge-to-edge distance between fibers.

In addition to polyurethane, other representative synthetic polymers useful for making electrospun fibers include, but are not limited to: silicones, carbonized polyurethane, nylon, polypropylene, polyethylene, polyester, polytetrafluoroethylene (PTFE), poly(lactic acid), poly(glycolic acid), polystyrene, polycarbonate, polyethylene glycol (PEG), fluoropolymers, poly(galactic acid), polyethylene terephthalate (PET), poly(dioxanone), poly(trimethylene carbonate) copolymers, poly (∈-caprolactone) homopolymers and copolymers, polyanhydrides, polyorthoesters, and copolymers of any of the foregoing. In addition to synthetic fibers, natural fibers, such as collagen and elastin, or non-synthetic fibers, such as silk, may be electrospun to make non-woven meshes in accordance with the invention.

Figure 2:
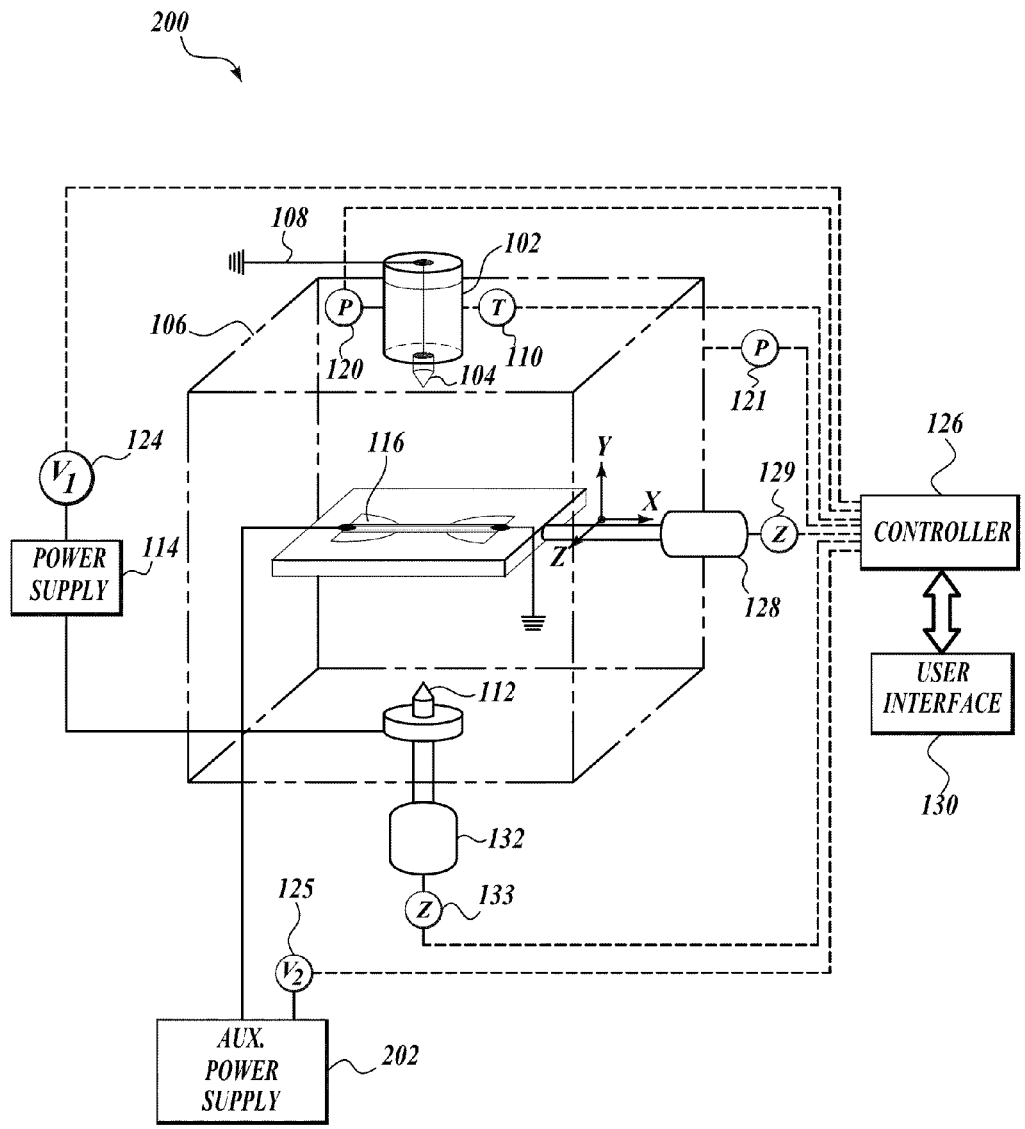
FIG. 2 is a diagrammatical illustration of an electrospinning apparatus in accordance with one embodiment of the present invention.

FIG. 2 is a diagrammatical illustration of a second embodiment of an electrospinning apparatus 200 in accordance with the present invention. The components of the electrospinning apparatus 200 that have the same numerical identification as the components illustrated in FIG. 1 are substantially the same and not mentioned for brevity. However, the electrospinning apparatus 200 illustrated in FIG. 2 additionally includes an auxiliary power supply 202 connected to the collection surface 116 at one end thereof. The opposite side of the collection surface 116 is connected to ground or at least to a lower potential than the opposite side so that the collection surface 116 generates a second electrostatic field. The power supply 202 voltage is measured by the voltage transmitter 125 that connects to controller 126. Accordingly, closed-loop control of the voltage 125 and of the electrostatic field strength generated by the power supply 202 is provided. The electrostatic field created as a result of the second power supply 202 is one means to cause interference with, manipulate and/or change the electrostatic field between the first 108 and the second 112 electrodes to produce non-woven meshes having controlled arrangements of fibers. Other means include the shape, size, design, and materials of construction of the collection surface 116. For example, as mentioned before, a collection surface 116 may include conductors aligned parallel to one another to create lines of electrostatic force parallel to the conductors. The second power supply 202 produces lines of force that cause the spun fibers to deposit in accordance with the lines of force of the electrostatic field. When fibers are spun from the reservoir 102, the fibers become aligned with the lines of the electrostatic field. This provides the opportunity for producing meshes containing non-random fibers. As fibers are deposited, the thickness of the mesh begins to increase, and the electrostatic field strength at the uppermost surface of the mesh decreases. Therefore, to continue to create patterns substantially similar as the first layers of fibers, the field strength is increased to account for the thickness of the deposited mesh. This produces the opportunity for creating three-dimensional matrices of fibers.

The apparatus of FIGS. 1 and 2 are used to produce non-woven meshes that may be incorporated into medical devices. The apparatus may be used to create a mesh having a fiber architecture that matches the native fibrillar structure (collagen and/or elastin) of the tissue that is to be replaced, so that the structural and mechanical properties of the medical device is similar. A problem with current tissue-engineered structures is that such matching does not exist, leading to a cascade of rejection problems. By using the versatility and control of the electrospinning apparatus described above, the desired architectures and mechanical properties can be achieved. Potentially, proteins, ligands, or other structures could be attached to the tissue-engineered structures to enhance performance.

As used herein, the term "medical device," and grammatical equivalents thereof, encompasses two types of devices: (a) a device that is completely or partially implanted into an animal body (such as a human body) during the course of normal operation of the device; and (b) a device that is used as a framework upon which to grow animal cells and/or tissues, either in vivo or ex vivo.

Representative examples of medical devices include, but are not limited to: prosthetic devices (such as artificial hip joints, artificial ligaments, artificial tendons and artificial knee joints), cardiovascular devices (such as vascular grafts, artificial heart valves and stents), drug delivery devices (e.g., non-implantable drug delivery devices or implantable devices that release one or more drugs over a desired time period), skin substitutes (such as dermal and epidermal scaffolds), scaffolds that support tissue growth (in such anatomical structures as bone, tooth, nerves, pancreas, eye and muscle), implantable biosensors (such as those used to monitor the level of drugs within a living body, or the level of blood glucose in a diabetic patient) and percutaneous devices (such as catheters) that penetrate the skin and link a living body to a medical device, such as a kidney dialysis machine. Some medical devices are completely implanted into an animal body (i.e., the entire device is implanted within an animal body), while some medical devices are partially implanted into an animal body (i.e., only part of the device is implanted within an animal body, the remainder of the device being located outside of the body). Examples of partially implanted medical devices include catheters and skin substitutes. Examples of medical devices that are completely implanted into a living body include stents, artificial heart valves and artificial hip joints. Some medical devices are used as a framework upon which to grow animal cells and/or tissues either in vivo or ex vivo.

The non-woven mesh created by the apparatus of the invention may be deposited directly onto the medical device, or can be formed separately and then attached to medical device, for example by using an adhesive. Representative examples of methods for attaching the non-woven mesh to a medical device include: physioadsorption; lamination with adhesives or heat fusion; electrocharging; static adhesion; "close encapsulation" by wrapping the mesh tightly to the material; covalent attachment via various complementary functional derivatization, e.g., carbodiimide coupling of amines on the medical device to carboxyls on the fibers; ionic derivatization via chemical modification to produce strong electrostatic interaction; and coordination chemistry to bond the mesh to metal via modification with thiols or phenanthrolines.

In another aspect, the present invention provides methods for manufacturing a medical device. The methods include a step of generating an electrostatic field between a first electrode and a second electrode, and electrospinning a dope through a nozzle onto a collection surface located between the first and second electrodes, wherein the collection surface influences the deposition of the fibers to lie in a pattern that matches the architecture and structure of a tissue that the mesh is supposed to replace. For example, the manufacturer can determine the fibrillar structure of the tissue, such as a heart valve, intended to be replaced or into which the medical device will be implanted, and then construct a collection surface using dielectric materials, conductive materials, or a combination of both, and then, optionally, with or without the addition of a second electrostatic field, the manufacturer is able to manipulate the electrostatic field so that the fibers that are spun are made to lie in an arrangement that resembles the native fibrillar structure. The non-woven mesh can be applied to a medical device by any method. For example, electrospun fibers can be deposited directly onto a medical device, or can be formed separately and then attached to a medical device, for example by using an adhesive. In other embodiments, the non-woven mesh is the medical device and can serve as a scaffold that allows collagen and cellular growth.

In one embodiment of the present invention, a medical device includes a non-woven mesh having arrays of non-random fibers and random fibers between arrays to attach adjacent arrays to one another. The medical device may include non-random fibers and random fibers having fiber diameters of about 5 µm to about 18 µm with a variability less than about 1.8%. The medical device may include non-random fibers and random fibers having interfiber spacing of about 4 µm to about 90 µm with a variability less than about 20.2%. The medical device may include non-random fibers and random fibers that are synthetic or natural fibers. The medical device may include non-random fibers and random fibers that are degradable fibers. The medical device may include non-random fibers and random fibers made from a polyurethane. The medical device may include non-random fibers and random fibers made from an amino acid-based polyurethane.

In another embodiment, the medical device includes a non-woven mesh made from fibers having fiber diameters of about 5 µm to about 18 µm with a variability of less than about 1.8% and interfiber spacing of about 4 µm to about 90 µm with a variability of less than about 20.2%. The medical device may include fibers that are synthetic or natural fibers. The medical device may include fibers that are degradable fibers. The medical device may include fibers that are made from a polyurethane. The medical device may include fibers that are made from an amino acid-based polyurethane.

In another embodiment, the medical device includes a non-woven mesh, wherein the non-woven mesh comprises randomly oriented fibers intermediate adjacent arrays of non-randomly oriented fibers, and wherein the randomly oriented fibers attach adjacent arrays.

In another embodiment, an implantable medical device includes a non-woven mesh having fibers arranged to have a fiber architecture similar to or that matches the fibrillar structure of tissue that the implantable device is intended to replace. The implantable medical device may include a mesh of arrays of non-random fibers and random fibers between arrays to attach adjacent arrays to one another. The implantable medical device may include fibers having fiber diameters of about 5 µm to about 18 µm with a variability less than 1.8%. The implantable medical device may include fibers having interfiber spacing of about 4 µm to about 90 µm with a variability less than about 20.2%. The implantable medical device may include fibers that are synthetic or natural fibers. The implantable medical device may include fibers that are degradable fibers. The implantable medical device may include fibers made from polyurethane. The implantable medical device may include fibers made from an amino acid-based polyurethane.

Another embodiment of the invention is an electrospinning apparatus. The electrospinning apparatus includes a reservoir for containing a spinning dope. The electrospinning apparatus includes a nozzle on the reservoir through which the spinning dope is extruded or drawn. The electrospinning apparatus includes an electrode in contact with a nozzle. The electrospinning apparatus includes a second electrode located a distance away from the first electrode. The electrospinning apparatus includes a power supply connected to at least one electrode to generate an electrostatic field between the first and second electrodes. The electrospinning apparatus includes a collection surface between the first and second electrodes that is isolated from the first and second electrodes to interfere with, manipulate, or cause a change in the electrostatic field. The electrospinning apparatus may include a collection surface that is made from a dielectric material. The electrospinning apparatus may include a collection surface that is made from a dielectric material and a conductive material. The electrospinning apparatus may include a collection surface that is made from a dielectric material and a conductive material, wherein the conductive material is connected to a second power supply to generate a second electrostatic field to interfere with, manipulate, or cause a change in the electrostatic field generated between the first electrode and the second electrode. The electrospinning apparatus may include a collection surface made from a conductive material so that fibers spun from the spinning dope align along the conductive material. The electrospinning apparatus may include a collection surface made from a dielectric material separating conductive materials aligned parallel to each other so that fibers spun from the spinning dope align into arrays of non-random fibers along the conductive materials and random fibers align between arrays so that the random fibers attach adjacent arrays to one another. The electrospinning apparatus may further include a controller and a user interface to control a parameter at a desired set point. An electrospinning apparatus may include a controller and an instrument to have closed-loop control of at least one variable measured by the instrument. The electrospinning apparatus may include means to control the temperature and/or the viscosity of the spinning dope. Such means may include a temperature transmitter, a controller and/or a means of heating, such as electrical heat tracing or coils filled with a hot fluid. The electrospinning apparatus may include means to control the pressure of the spinning dope. Such means may include a pressure transmitter, a controller and lines connected to a pressure and/or a vacuum source, so as to pressurize and/or apply vacuum at the reservoir. The electrospinning apparatus may include means to control the distance between the first electrode and the second electrode. Such means may include a controller and a translation stage that has a actuatable arm which supports one electrode so that linear motion of the arm causes a decrease in the distance between the first and second electrodes. The electrospinning apparatus may include means to control the distance of the collection surface from the nozzle. Such means may include a controller and a translation stage connected to the collection surface via an arm and an actuator that actuates the arm to narrow the distance between the collection surface and the nozzle. The electrospinning apparatus may include means to control voltage generated by the power supply. Such means may include a voltage transmitter and a controller so that the voltage at one electrode is controlled.

Another embodiment of an electrospinning apparatus includes a first and a second electrode between which an electrostatic field is generated, and a collection surface isolated from and located between the first and the second electrodes that causes interference with or changes the electrostatic field, wherein fibers that are deposited on the collection surface are made to lie in a pattern according to the interference or changes in the electrostatic field. The electrospinning apparatus may have the collection surface made from a dielectric material. The electrospinning apparatus may have the collection surface made from a dielectric material and a conductive material. The electro spinning apparatus may have the collection surface made from a dielectric material and a conductive material, wherein the conductive material is connected to a power supply to generate a second electrostatic field to interfere with, manipulate, or cause a change in the electrostatic field generated between the first electrode and the second electrode. The electrospinning apparatus may have the collection surface made from a conductive material along which fibers spun from the spinning dope align. The electro spinning apparatus may have the collection surface include dielectric material separating conductive materials aligned parallel to each other so that fibers spun from the spinning dope align into arrays of non-random fibers and random fibers between arrays to attach adjacent arrays to one another. The electrospinning apparatus may include a controller and a user interface to control a controlled parameter at a desired set point. The electrospinning apparatus may include a controller and an instrument to have closed-loop control of at least one variable measured by the instrument. The electrospinning apparatus may include a supply of spinning dope and means to control the temperature and/or viscosity of the spinning dope. The electrospinning apparatus may include a supply of spinning dope and means to control the pressure of the spinning dope. The electrospinning apparatus may include means to control the distance between the first electrode and the second electrode. The electro spinning apparatus may include a nozzle through which fibers are produced and means to control the distance of the collection surface from the nozzle. The electrospinning apparatus may include a power supply and means to control voltage generated by the power supply. The electrospinning apparatus may include a controller and two or more instruments to have closed-loop control of two or more variables measured by the instruments.

Another aspect of the invention is a method for making a non-woven mesh for a medical device. The method includes generating an electrostatic field between a first electrode and a second electrode. The method includes electrospinning a dope through a nozzle onto a collection surface located between the first electrode and the second electrode, wherein the collection surface causes interference with, manipulates, or changes the electrostatic field, wherein fibers that are deposited on the collection surface are made to lie in a pattern according to the interference, manipulation, or changes in the electrostatic field caused by the collection surface. The method may include having a collection surface made from a dielectric material. The method may include having a collection surface made from a dielectric material and a conductive material. The method may include having a collection surface made from a dielectric material and a conductive material, wherein the conductive material is connected to a second power supply to generate a second electrostatic field to interfere with, manipulate, or cause a change of the electrostatic field generated between the first electrode and the second electrode. The method may include having a collection surface made from a conductive material along which fibers spun from the spinning dope align. The method may include having a collection surface made from a dielectric material separating conductive materials aligned parallel to each other, wherein the fibers spun from the spinning dope align into arrays of non-random fibers along the conductive materials and random fibers align between the arrays along the dielectric material to attach adjacent arrays to one another. The method includes controlling a parameter at a desired set point. The method may include providing for closed-loop control of at least one variable. The method may include controlling the temperature and/or the viscosity of the spinning dope. The method may include controlling the pressure of the spinning dope. The method may include controlling the distance between the first electrode and the second electrode. The method may include controlling the distance of the collection surface from the nozzle. The method may include controlling the voltage at least at one of the electrodes.

In another embodiment of an electrospinning method, the method includes spinning fibers from a dope onto a collection surface producing lines of force, wherein the lines of force correspond to a fibular structure of any mammalian or animal tissue. The method may include applying a potential across the collection surface to generate the lines of force.

EXAMPLE 1

A Representative Electrospinning Apparatus And Method

An electrospinning apparatus was constructed containing a polymer chamber, first and second electrodes, an enclosure, a collection surface, and an x-y-z translation stage.

The polymer chamber held 16 cc of polymer melt at a controlled temperature and pressure. The chamber was heated via band heaters (model NHW00158, Tempco, Wood Dale, Ill.) placed around the outer surface of the chamber. Temperature was monitored using platinum resistance temperature transducers (RTD) (model 1PT100KN815, Omega, Stamford, Conn.) embedded in the bottom of the chamber. A pressure control valve (IP413-020, Omega) and a vacuum control valve (PV104-5V, Omega) were connected to ports on the top of the chamber, and pressure and vacuum sensors (PX142-030D5V, PX141-015V5V, Omega) were located in the lines between the control and chamber ports. Temperature, pressure, and vacuum were controlled via closed-loop controllers as described below. A grounded electrode was positioned within the polymer melt chamber, extending out through an upper port. A stainless steel nozzle with a length to diameter ratio of 4.5 was positioned on the bottom of the chamber so that polymer emerging from the chamber entered the enclosure. The polymer chamber was mounted on top of the polycarbonate enclosure via high temperature thermoplastic mounting brackets. The mounting brackets were designed such that only the nozzle was exposed to the interior of the enclosure. Iris ports on each side prevented airflow from affecting the electrospinning process yet allowed easy entry into the enclosure. When assembled, the polymer chamber was sealed except for the inlets for pressure and vacuum control.

The positive electrode was mounted to a Delrin carriage within the enclosure. The carriage was connected to a 0.8-mm lead screw so that electrode distance from the nozzle could be easily adjusted. A high-voltage power supply (RP-50-100, Del, Valhalla, N.Y.) connected between the positive and ground electrodes provided a controllable potential difference from 0 to 50 kV.

The collection surface was mounted to an x-y-z stage (404150XR, Parker Daedal, Harrison City, Pa.) via a polycarbonate arm that protruded into the enclosure through a port in the rear. An accordion boot formed a seal between the arm and the enclosure. All components within the enclosure were constructed from dielectric materials with the exception of the nozzle and the positive electrode.

Controller

A Labview (National Instruments, Austin Tex.) virtual instrument (VI) was used to control the temperature, voltage, vacuum/pressure behind the melt, and stage position. For temperature measurement, signals from the RTDs were converted to voltages with signal conditioning modules (OM5-IP-600-C, Omega, Stamford, Conn.), digitized with a multi-function data acquisition board (PCI-MIO-16XE-10, National Instruments, Austin Tex.), and monitored on a PC (450 mHz Optiplex GX1, Dell, Round Rock, Tex.). To control the duration of heating so as to achieve set point temperatures, pulse-width-modulated digital outputs from the controller were sent to solid-state control-output modules (ACO5-C, Omega, Stamford, Conn.). The duty cycle was determined using the average temperature as a percentage of the set point. Lower percentages increased the duty cycle.

Vacuum and pressure were controlled with a proportional closed-loop feedback control scheme. Signals from the vacuum sensor and pressure sensor were digitized and monitored on the PC. Signals sent to the vacuum control valve and pressure controller were proportional to the differences between the set points and their respective instantaneous values. A greater difference increased the time the valves were open.

Components from a library of Labview virtual instruments (Motion Toolbox™, Parker Compumotor, Rohnert Park, Calif.) were embedded in the VI for motion control of the x-y-z stage. Control command inputs from the VI were sent to an AT6400 four-axis controller (Compumotor) that converted the data for use in a step indexer (Zeta4, Compumotor). On initialization all axes were positioned with respect to a known position. Monitoring the position with the AT6400 allowed for pseudo-feedback control of axis position.

Mesh Production and Analysis

An analysis of the system parameters was performed using meshes electrospun from a melt. Melt spinning was chosen over solvent spinning so as to reduce inconsistencies related to solvent evaporation rates and solution concentration changes that can result during electrospinning from solution.

Controlled Parameters

In this electrospinning apparatus there were three classes of variables to consider: the device specific variables, the polymer specific variables, and the collection surface specific variables. The primary device specific variables were the applied voltage (V), distance from the electrode to the nozzle (De), nozzle length (Nl), and nozzle diameter (Nd) (Note: the nozzle is usually referred to as a capillary in the electrospinning literature). A consistent Nl:Nd ratio of 4.5 was used. The only polymer specific variable considered for melt spinning was the polymer viscosity. Viscosity of the melted polymer was dependent on the melt temperature (T) and since temperature was easily controlled in this system, temperature was used as the parameter instead of viscosity. The collection surface specific variables were dielectric strength (DS) and surface area (SA).

A separate experiment was conducted to determine if viscosity did indeed decrease when melt temperature increased. 5.75 g of polymer was placed in a nozzle-shaped chamber of 2 mm diameter and 11.73 mm length. The nozzle was heated in the thermally-controlled melt chamber described above and brought up to a specified temperature—225, 234, or 243° C.—over a 15 min interval. Polymer was collected for a 5 min interval and then weighed. Viscosity was calculated as the ratio of the shear stress at the nozzle wall to the apparent shear rate at the nozzle wall:

$$\eta_a = \frac{\Delta P}{L} \frac{\pi R^4}{2Q}$$

where, $\Delta P$ is the pressure gradient across the nozzle ($\rho g*(H+L)$), H is the average height of polymer above the nozzle, L is the nozzle length, R is the nozzle diameter, and Q is the volumetric flow rate ($M/(\rho T)$). The polymer density ($\rho$) was determined experimentally by weighing a precise volume of molten and condensed polymer, ensuring it was free of all air bubbles. Three trials were conducted at each temperature. A test statistic of 0.05 was used to make comparisons between groups.

In this device, the distance between the collected fibers and the nozzle was independent of the electrode position. Thus, the device specific parameter of collection surface distance from the nozzle (Ds) was also considered. This parameter was normalized to De for consistent comparison between values of De (Ds/De=$\eta$). For analysis of the electrospinning parameters of electrode distance (De), ratio of collection surface distance to electrode distance ($\eta$), applied voltage (V), and temperature (T), polystyrene Petri dishes (100 mm diameter; 15 mm depth) were used for the collection surface. To determine the effect of the collection surface dielectric strength (DS), additional tests were conducted using Teflon™, Pyrex™, and additional polystyrene Petri dishes (0.8 mm thickness and 1.75 mm thickness). More tests using 150 mm×15 mm polystyrene Petri dishes were conducted to analyze the effect of collection surface area (SA) on the end product mesh. TABLE I summarizes the experimental parameters and the ranges over which they were varied and analyzed. For most of the parameters these values also represent the range over which the electrospun jet was stable enough to collect fibers. The upper and lower bounds for η, V, and T were determined by systematically changing the parameter within a 170 mm electrode spacing range until a consistent mesh could no longer be collected. The upper and lower bounds for De were established using the upper and lower bounds for η and systematically changing De until a consistent mesh could no longer be collected.

The interactions between variables were assessed. All parameters other than those under study were held constant for each of these evaluations: The ratio η was varied at three levels within five levels of De. V was varied at three levels within three levels of η and three levels of De. T was varied at three levels within three levels of η. The collection surface dielectric strength was varied at four levels within three levels of η. The collection surface area was varied at two levels within three levels of η.

The mass flow rate was measured for a subset of the test parameters. The subsets were as follows: Measurements were made at five levels of De, three levels of V, three levels of η, and two levels of SA. Thus, a total of 75 interactions were evaluated.

Mesh Collection

To conduct the analysis, meshes were manufactured from thermoplastic polyurethane (Estane™ 58315, Noveon, Cleveland, Ohio) while each parameter was varied. For analysis of the device specific parameters, to assure that the temperature of the melt was consistent throughout testing, the following protocol was used for each test. Approximately 5 g of polymer was placed in the electrospinning melt chamber and heated until a slow steady flow emerged from a 1 mm nozzle at atmospheric pressure (~15 min). Once the flow was steady, the nozzle tip was cleaned. When a fresh droplet formed on the tip, voltage was applied between the polymer drop and the positive electrode, electrospinning a continuous fiber from the nozzle. The continuous fiber was collected on a surface (inverted Petri dish) that was positioned between the nozzle and the positive electrode. To analyze the polymer specific parameter (related to polymer viscosity), electrospinning was conducted at different polymer temperatures.

To ensure a consistent thickness sample, during electrospinning the collection surface was translated in the horizontal plane in concentric circles and decreasing diameter at a rate of 5 mm/s. Fiber collection began at the outer edge of the surface and then the circle diameter was decreased in 2 mm increments until the center of the surface was reached. Fiber collection was continued while the surface returned to the original position in increasing diameter concentric circles. Sample thickness average 0.3 mm.

To determine the mass flow rate, fibers were collected for 300 s, and then the sample mass was measured. Care was taken such that all fibers were collected on the surface throughout the tests. The mass flow rate was the sample mass divided by 300 s.

Mesh Analysis

Since the focus of this research was to produce predictable and repeatable scaffolds for biomaterial and tissue engineering applications, an appropriate method needed to be developed to analyze the end product mesh. The properties of the mesh of interest were the fiber diameter and interfiber spacing. Samples of each manufactured test mesh were mounted on 14 mm OD, 12 mm ID Teflon frames using Titebond™ polyurethane glue (Franklin International, Columbus, Ohio). Care was taken to prevent straining the sample during the mounting process. The samples were embedded in dyed OCT (Tissue-Tek, Sakura, Calif.) and flash frozen. The OCT was dyed to enhance the contrast between the translucent OCT and translucent polymer fibers so as to simplify image processing. For each sample 20 consecutive, 5-μm thick sections were taken perpendicular to the horizontal plane of the sample and placed on glass slides for light microscopy analysis. At least 16 images from the first, last, and two intermediate sections from each sample series were taken. The images were digitized using Image Pro Plus™ (Media Cybernetics, Silver Spring, Md.) then analyzed using custom algorithms written with the Image Processing Toolbox in Matlab™ (Mathworks, Natick, Mass.).

To assess fiber diameter a semi-automated method was used. The digitized images were imported, converted to grayscale, and thresholded such that only the fiber cross-sections remained in the image. Specs resulting from inconsistencies in the embedding medium were removed. To determine the appropriate threshold level for each image, algorithms in the Matlab image processing toolbox were used. The algorithms, based on an intensity level specified by the user, identified peaks and valleys in the image and filled in enclosed regions. Once the user was satisfied with the image processing, the properties of each region (fiber) were determined.

The properties of each fiber were determined using the regional properties algorithms in the Matlab image processing toolbox. An ellipse was fit to each fiber cross-section, and the minor axis length was determined. The minor axis length was considered to be the fiber diameter. An average interfiber spacing was determined using the stereological relationship for the mean free distance between particles in a two dimensional plane, wherein the equation: $L=0.5(N_A)^{-1/2}$, describes the stereological relationship of the distance (L) between two objects in a two-dimensional space. The interfiber spacing was defined as the edge-to-edge distance between fibers.

Results

Parameterization

ANalysis Of VAriance between groups (ANOVAs) performed on the data revealed that there was a significant ($p<0.05$) effect for all test parameters with respect to fiber diameter and interfiber spacing. Below, parameters are expressed normalized to their maximum tested values. The range of testing within a parameter was limited by the stability of the electrically spun jet. For the distance between electrodes (De), fibroporous meshes outside of the indicated parameter range (TABLE I) could not be collected. Fibroporous meshes could not be collected at voltages (V) less than 25 kV. Voltages above 35 kV resulted in highly unstable jets which could only be collected at De=170 and η=0.39. For all combinations of De and V, meshes could be collected only within the range for η indicated in TABLE I. Temperatures below 225° C. resulted in polymer melts that were too viscous to spin whereas temperatures above 243° C. overheated the polymer. The collection surface values were limited by the availability of acceptable Petri dishes for fiber collection. Data presented below are for the parameter combination within each test variable which had the greatest influence on the fiber diameter and interfiber spacing.

Viscosity testing at controlled temperatures showed that viscosities at 225° C., 234° C., and 243° C. averaged 678.3 (+149.9), 136.2 (+35.2), and 53.8 (+4.5) cP, respectively. The viscosity at 225° C. was significantly larger than that at 234° C. or 243° C.; the viscosity at 234° C. was significantly larger than that at 243° C. ($p<0.05$).

Figure 10:
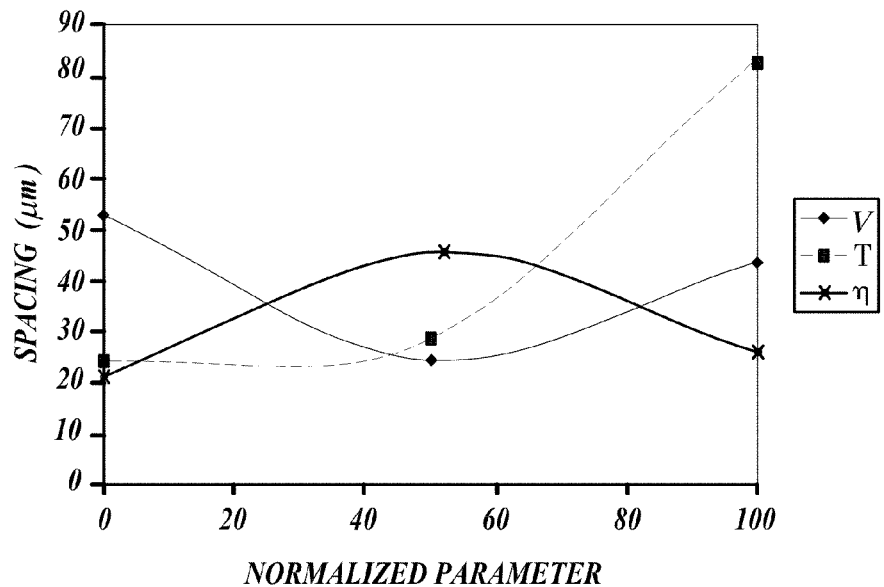
FIGS. 10 and 11 are graphs representing the interfiber spacing dependence on voltage (V), temperature (T), ratio of collection surface distance from nozzle to distance between the electrodes ($\eta$), surface area (SA), dielectric strength (DS), and distance between the electrodes (De)
Figure 11:
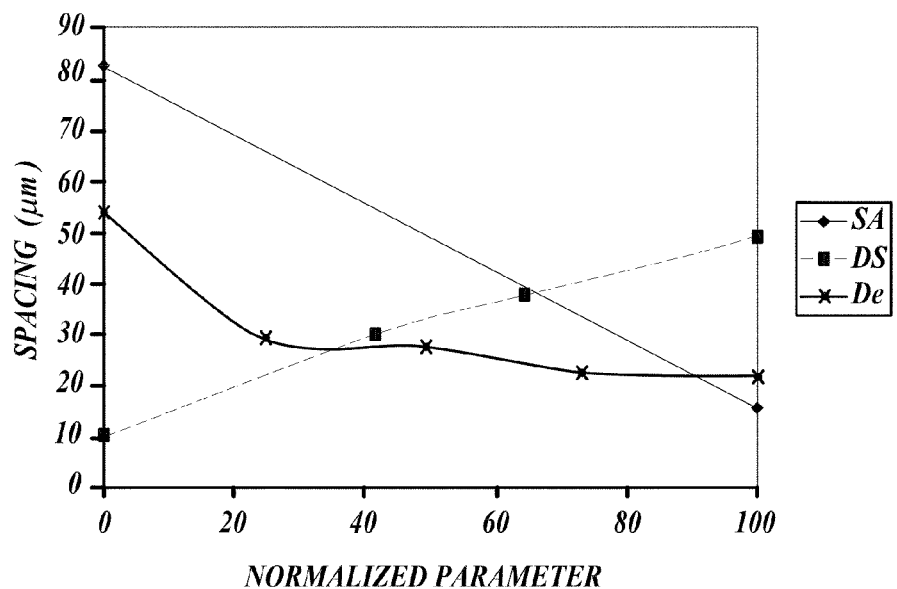

Increasing the temperature (T) (which decreased the viscosity) caused an increase in fiber diameter (FIGS. 10, 11). A concave curve related fiber diameter to applied voltage. Both temperature and applied voltage had less effect on fiber diameter compared with features of the collection surface, i.e. dielectric strength and surface area. The dielectric strength (DS) and surface area (SA) had opposing effects. The diameter increased with increasing dielectric strength, whereas the diameter decreased with increasing surface area. Fiber diameter was nonlinearly related to distance from the nozzle (De).

Figure 12:
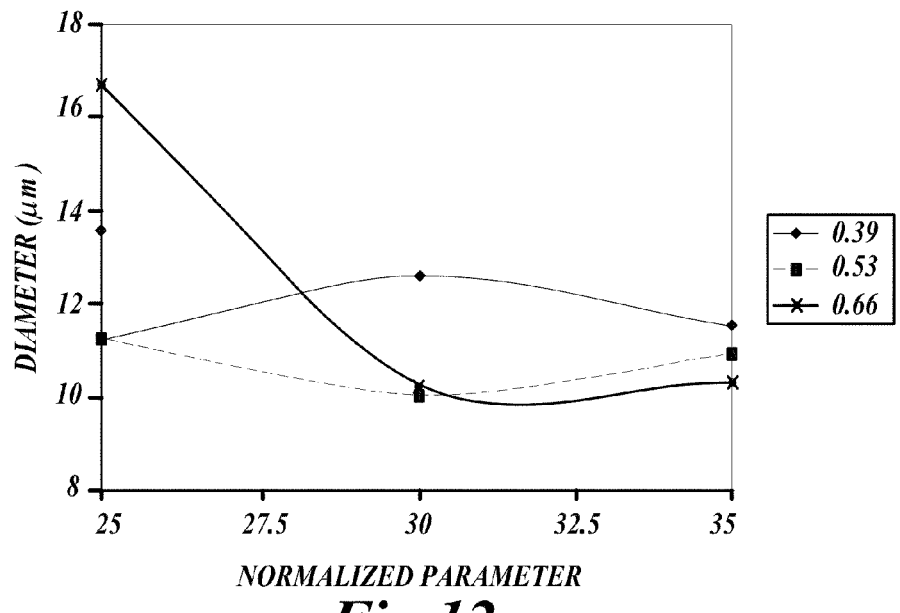
FIG. 12 is a graph representing the fiber diameter dependence on the voltage (V) for three different values of the ratio of collection surface distance from nozzle to distance between the electrodes ($\eta$)
Figure 13:
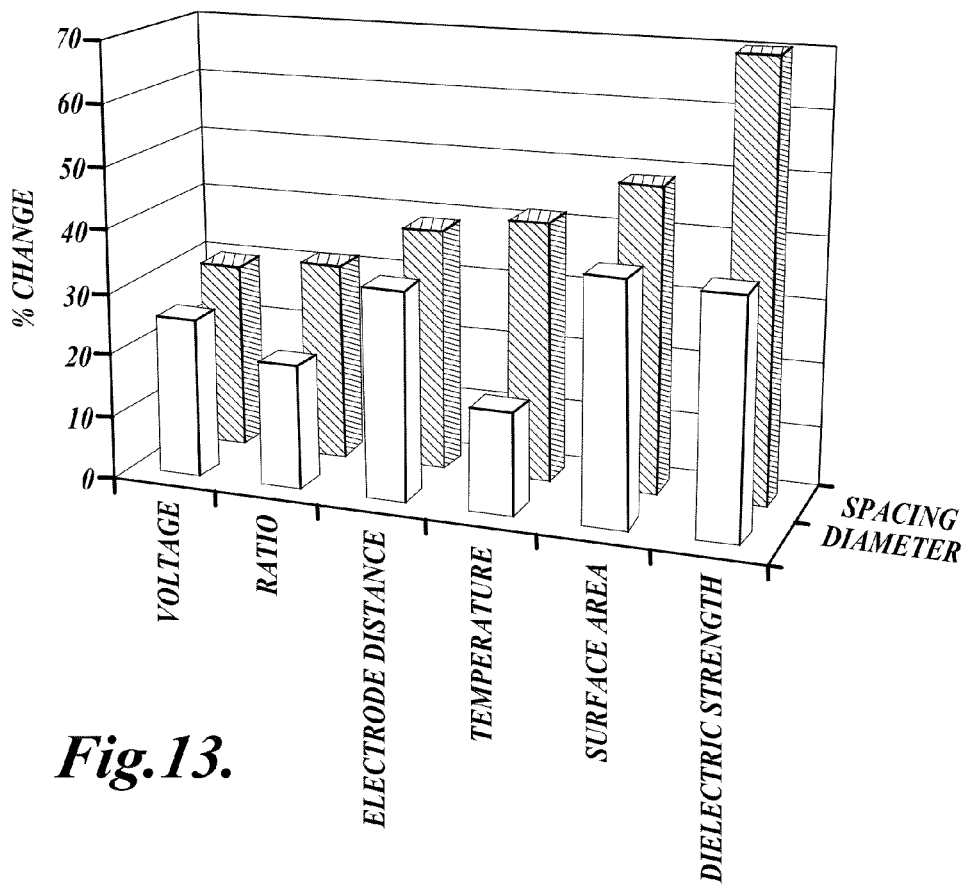
FIG. 13 is a bar graph representing the relative influence of voltage (V), temperature (T), ratio of collection surface distance from nozzle to distance between the electrodes (η), surface area (SA), dielectric strength (DS), and distance between the electrodes (De)

Interfiber spacing increased with increasing temperature but was not strongly dependent on applied voltage (FIGS. 12, 13). The surface area of the collection surface had the most significant effect of all parameters tested, decreasing with interfiber spacing. The collection surface dielectric strength's effect was to increase interfiber spacing. Both distance between the electrodes and the ratio between electrode distance and collection surface distance exhibited nonlinear trends with respect to interfiber spacing.

The complexity of the interdependence of parameters is exemplified in FIG. 12. Holding the electrode distance constant and varying the collection surface to electrode distance ratio resulted in three different trends for the dependence of fiber diameter on applied voltage. Only the high ratio ($\eta=0.66$) showed a strong relationship. The other two ratios ($\eta=0.53$ and $0.39$) had a concave curve and a convex curve, respectively.

The average percent change of fiber diameter and interfiber spacing for all parameter tests is shown in FIG. 13. Applied voltage and viscosity (controlled by temperature) did not have the greatest influence (indicated by average percent change) on fiber diameter and interfiber spacing. Within the six parameters of interest, the collection surface had the greatest impact on fiber diameter and interfiber spacing. The dielectric strength of the collection surface induced the greatest change, and the collection surface area induced slightly less of a change in both parameters.

The effects of the parameters were compared quantitatively. The average percent change in fiber diameter was at least 14% and 15% greater for dielectric strength and surface area respectively than for any other parameter. For interfiber spacing the induced change was at least 34% and 13% greater for dielectric strength and surface area, respectively. To determine if the difference in percent change was significant student-t tests were performed. The null hypotheses were that the percent change in fiber diameter and interfiber spacing induced by one of the four parameters voltage (V), distance between the electrodes (De), temperature (T), or the ratio ($\eta$) was not different from the change induced by the collection surface dielectric strength (DS) or surface area (SA).

The percent change in fiber diameter induced by DS and SA was significantly ($p<0.05$) different from the change induced by V, T, or $\eta$. However, it was not significantly different from that induced by De. DS induced a greater change in interfiber spacing than V, T, or $\eta$. The change induced by SA on interfiber spacing was not significant with respect to the change induced by the other parameters.

Figure 14:
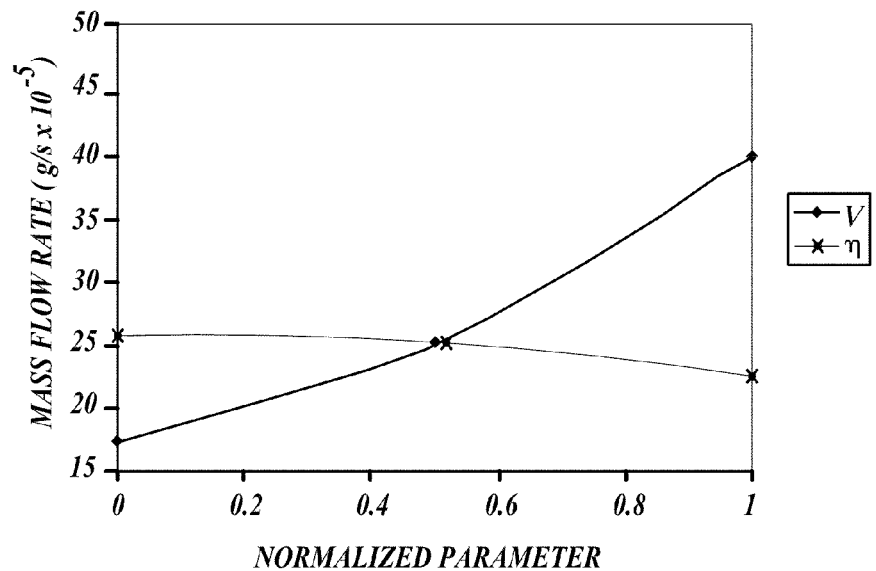
FIGS. 14 and 15 are graphs representing the mass flow rate dependence on voltage (V), ratio of collection surface distance from nozzle to distance between the electrodes (η), surface area (SA), dielectric strength (DS), and distance between the electrodes (De)
Figure 15:
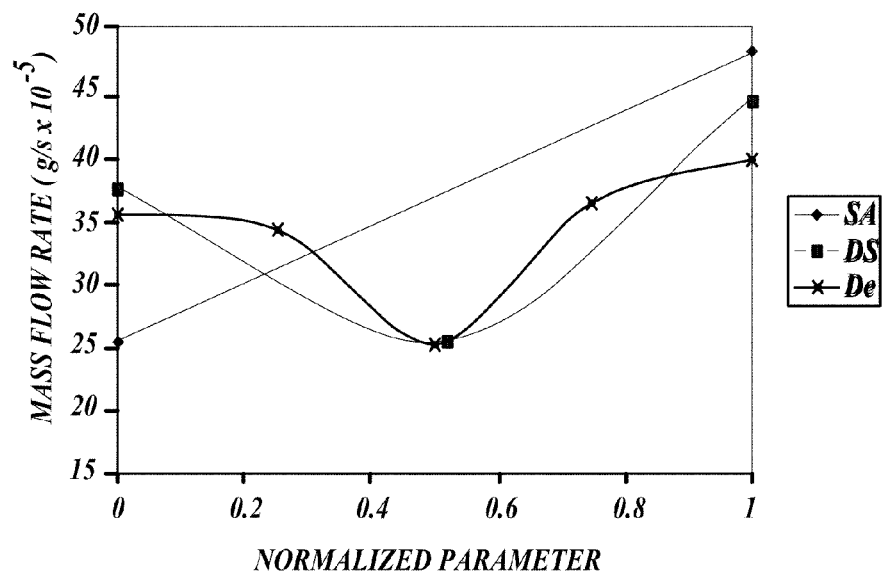

The mass flow rate decreased slightly with increasing $\eta$ and increased with increasing voltage. Increasing SA increased the mass flow rate while increasing DS resulted in a parabolic relationship with the mass flow rate (FIG. 14). An increase in mass flow rate would be expected to increase fiber diameter.

Correlations between the mass flow rate and fiber diameter, and mass flow rate and interfiber spacing were analyzed to further investigate the relationships among the parameters. TABLE II shows the correlation coefficient for mass flow rate (MFR) verses fiber diameter and interfiber spacing for all test parameters except one held constant ($\eta$, DS, or V). MFR was well-correlated to the fiber diameter for $\eta$ and V but not for DS. The interfiber spacing correlated poorly with MFR for all three test parameters.

Repeatability, Predictability, and Accuracy

The smallest average fiber diameter achieved for an electrospun mesh had a diameter of $5.32\pm2.71$ μm and the smallest average interfiber spacing achieved was $4.39\pm1.41$ μm. Repeatability for scaffold production has a mean error of 1.8% and 20.2% for fiber diameter and interfiber spacing, respectively. On all repeated sample tests combined there was no significant difference for diameter ($p=0.39$) over the range of 8.63 μm to 14.13 μm or for spacing ($p=0.20$) over the range of 44.75 μm to 82.85 μm.

Discussion

The fiber diameter range and interfiber spacing range were dependent on the polymer selected, the viscosity control method (melting) used, and the collection surface material. Contrary to the literature, the fiber diameter increased when the applied voltage was increased. Results for the correlation between polymer temperature (inversely related to viscosity as confirmed by the viscosity tests reported here) and fiber diameter are also inconsistent with the literature. Generally, it is expected that the fiber diameter decreases with increased temperature because the polymer viscosity is decreased thus the strain rate is increased. However, if the viscosity becomes sufficiently low, the frictional forces in the fluid are no longer a factor, and the mass flow rate will increase with increased temperature, resulting in an increase in fiber diameter. The collection surface had the most significant effect on fiber diameter of the parameters investigated because of its effect on the electric field. The collection surface was independent of the electrodes, and the collection surface was positioned between the electrodes. The collection surface likely distorted the electric field (FIG. 17), causing it to deflect around the surface, thus causing a change in voltage.

The physical size of the collection surface also affected the electric field between the electrodes. Placing a dielectric between the electrodes deflected the electric field. Increasing the surface area of the collection surface increased the degree of field deflection. This would tend to increase the secondary instability of the spinning jet, which would result in smaller fiber diameters. In addition, increasing the secondary instability (hence wave propagation frequency) decreased the mesh interfiber spacing, as confirmed in TABLE 2.

The repeatability achieved with this system of 1.8% for fiber diameter and 20.2% for interfiber spacing are expected to be within the needs for tissue engineering applications. Consistent fiber diameters may be important to tissue response, and a consistent architecture will ensure meshes with relatively uniform mechanical properties without locally weak regions.

TABLE I

ANALYZED PARAMETER VALUES

| Parameter | Analyzed Values | | | | |
|---|---|---|---|---|---|
| De (mm) | 130 | 150 | 170 | 190 | 210 |
| $\eta$(mm/mm) | 0.39 | 0.53 | 0.66 | | |
| V (kV) | 25 | 30 | 35 | | |
| T (C.) | 225 | 234 | 243 | | |
| DS (kV) | 1 | 54 | 84 | 126 | |
| SA (mm$^2$) | 6082 | 15394 | | | |

TABLE II

CORRELATIONS OF FIBER DIAMETER AND INTER-FIBER SPACING WITH MASS FLOW RATE WITH ALL PARAMETERS EXCEPT ONE HELD CONSTANT

| Parameter not Held Constant | Fiber Diameter | Inter-Fiber Spacing |
|---|---|---|
| η | 0.97 | 0.39 |
| DS | 0.21 | −0.06 |
| V | 0.84 | 0.35 |

EXAMPLE 2

A Representative Method of Making a Medical Device

Scaffold Production

This example demonstrates the making of a scaffold with the architecture and mechanical properties of a representative region of a mitral valve anterior leaflet. One scaffold type that had a linear stress strain relationship similar to the pre-transition region and a second scaffold type that had a biphasic relationship similar to the native tissue were developed. The scaffolds were produced using an electrospinning apparatus substantially as described above.

Two formulations of degradable polyurethane (DPU) were used to produce scaffolds with similar architectures and different mechanical properties. Each polymer formulation was solvated in chloroform to a specific % wt/v in sealed glass vials to prevent evaporation of the solvent. The first formulation (DPU5050) was 50% Woodhouse PCL530 and 50% Woodhouse PCL1250 solvated in chloroform to achieve a 36% wt/v. The second formulation (DPU1250) was 100% PCL1250 solvated in chloroform to achieve a 25% wt/v. The polymers were solvated under continuous mixing for a minimum of 24 hrs before use and were stored while mixing continuously.

The solvated polymer solution (either DPU5050 or DPU1250) was placed into a 10 ml glass syringe. The syringe was placed into a syringe pump which was used to control the polymer feed rate at ~0.001 ml/min. Between 15 and 20 kV was applied between the electrodes while the collection surface was simultaneously charged with 5 to 10 kV. The collection surface was translated in a predefined pattern in the x-y plane and the fibers were collected on the surface.

Collection Surface Design

The collection surface was constructed as described in the following paragraph for all test samples. Dumbbell-shaped sections as illustrated in FIG. 3 measuring 15 mm at the ends, 2.5 mm at the narrowest section, 20 mm in length over the narrow central section and having an overall length of 50 mm were cut from adhesive backed copper sheets. The dumbbell-shaped sections were adhered to 25 mm×75 mm×1 mm, pre-cleaned, superfrost plus slides (48311-703, VWR Scientific, West Chester, Pa.). The dumbbell was aligned on the slide such that one end of the dumbbell was approximately 5 mm from the uncoated end of the slide. On the central region of the copper dumbbell-shaped section an additional 2 mm×20 mm adhesive backed Teflon section was placed on top of the copper section. A fiber aligner was used to place parallel 40 gauge copper wires over the central region of the templates aligned with the long axis of the slide. The wires were glued to the slide at each end of the template using cyanoacrylate and allowed to dry overnight. Once the wires were securely adhered to the slide, the ends of the wires were twisted to form a bundle and soldered. The number of wires and the spacing between the wires was analyzed for consistency of wire placement using light microscopy.

Prior to spinning on the template, the templates were cleaned in 70% ETOH and a sterile wire screen with a window cut in the middle was slid over the slide such that the window was centered over the central region of the template. The wire screen made removing the scaffold easier.

Four to six passes were made through the electrospinning jet to assure even coverage over the central region of the template. Once the central region was covered, the template was positioned to reinforce the transition region where the screen interfaces with the scaffold. Once complete, the template with the scaffold still attached was placed in a −20° C. freezer to dry for two days. At least four scaffolds were produced for each in vitro test.

Spinning Technique

The electrospinning technique employed is referred to as the modified point-point spinning technique. Briefly, the modified point-point spinning technique was designed to take advantage of contact and non-contact electrical manipulation of the spinning fiber. The objective was to achieve parallel arrays of electrospun fibers with controlled spacing, randomly oriented fibers between the arrays. This architecture was chosen to mimic the parallel collagen structure of the native valve while allowing cellular ingrowth between the arrays.

To achieve this architecture, the template was clamped in the holder on a 3-axis stage. An auxiliary power supply was connected to the soldered copper wire. The template was positioned between the positive electrode and the grounded stainless steel pipetting needle. High voltage was then applied between the electrodes and to the template. The polymer solution was pumped through the nozzle at a rate of 0.001 ml/min while the stage was systematically translated in the x-y plane.

Valvular Tissue Engineering

Cell Harvest and Culturing

Tissue was harvested from a juvenile female swine immediately following euthanasia. The mitral valve anterior leaflet tissues were harvested. Endocardial cells were removed where possible by scraping with a scalpel blade and the tissue samples were cut into ~1 mm pieces. Pieces were washed in phosphate buffed saline (PBS) and centrifuged for 10 minutes at 1000 rpm. Tissue samples were cultured in 100 mm Petri dishes in Delbucco's Modified Eagles Medium (DMEM), supplemented with 10% FBS, and 1% antibiotic/antimycotic. The first passage of the cells was 17 days after harvest. One week after the first passage of cells, the cells were cryopreserved for later use. Prior to seeding scaffolds, all cells were reanimated and cultured for at least 2 weeks.

Cytotoxicity and Endotoxicity Evaluation

Prior to seeding the DPU scaffolds, cytotoxicity and endotoxicity tests were conducted on representative samples of the material. An elution test was performed on polymers that had recently been produced based on the United States Pharmacopia (USP) 24 guidelines for In Vitro Biological Reactivity Tests. The samples were prepared for the elution as follows.

The dumbbell collection surface (template) was installed in the holder and connected to the auxiliary power supply. A 25% wt/v solution of DPU5050 in chloroform was prepared and electrospinning was initiated as described in the previous sections. Once the collection surface was completely covered, the sample was removed from the template and placed in a Petri dish. This process was repeated until at least 0.2 grams of mesh was produced.

The samples were washed with RBS 35 detergent solution for 30 minutes, then rinsed three times with deionized water for 5 minutes each wash. Samples were dried in the laminar flow hood overnight. Once the samples were dry, they were UV sterilized for 30 minutes on each side in an uncovered Petri dish. Once sterile, samples were aseptically transferred to a sterile, non-pyrogenic, polystyrene tube (Falcon, 2003). Samples were submerged in 1 ml DMEM and eluted for 24 hours in an incubator (37° C., 5% $CO_2$). After 24 hours, a standard cytotoxicity protocol was followed.

Endotoxin evaluation was performed by preparing the samples as previously described. The samples were aseptically transferred to sterile, non-pyrogenic tubes and submerged in 1.0 ml LRW reagent water such that the sample concentrations equal 100 mg/ml. The samples were incubated overnight at 37° C. and 5% $CO_2$ concentration. After incubation, a standard endotoxicity protocol was followed.

DPU Scaffold Preparation and Seeding

After 2 days in the freezer, the scaffolds were placed in the laminar flow hood and excess material removed from around the template. The screen and scaffold were removed from the template, being careful not to damage the scaffold. Once the scaffold/screen assembly was removed, the unit was UV sterilized for 30 minutes on each side. Sterile 3.175 mm×25.4 mm stainless steel dowel pins were placed on the scaffold ends by bending the screen tabs around the pins and bending the screen ears to lock the tabs in place.

For each experiment, two scaffolds were placed in 150 mm Petri dishes such that the scaffold was not in direct contact with the dish and submerged in a 50 µg/ml concentration of laminin. The remaining scaffolds were placed in 150 mm Petri dishes and submerged in PBS for use as unseeded controls. All dishes were sealed with parafilm to prevent laminin evaporation and placed in the refrigerator overnight to enhance laminin attachment to the scaffold.

After 24 hours of refrigeration, the scaffolds were removed from the laminin or PBS and placed in 10 ml to sterile PBS in clean/sterile Petri dishes. PMVIV cells were removed from the incubator, trypsinized, suspended in 10 ml culture media, and centrifuged for 10 minutes at 1000 rpm. The supernatant was removed after centrifuging and the cells resuspended in 500 µl culture media. The cells were counted using a direct counting method and a sufficient volume of cell suspension was placed on the scaffolds to achieve seeding with approximately $1\times10^6$ cells. The seeded scaffolds were placed in the incubator for 30 minutes to 1 hour to allow for cell attachment after which 10 ml of media was added to the culture dish. The control scaffolds received the same treatment substituting an equal volume of culture media for the cell suspension. All scaffolds were incubated for 7 days, exchanging 5 ml of media every two days. For all tests, two of four scaffolds were seeded and two scaffolds, one seeded and one unseeded, were uniaxially strained for 1 hour per day for up to 5 days.

Tissue-Engineered Construct Mechanical Conditioning

To accomplish in vitro mechanical conditioning of the seeded constructs, a uniaxial bioreactor was constructed that would interface with a custom testbed that was described in the literature. [Mitchell, S. B., *A Device to Biaxially Strain Biomaterials in Culter*, in *Bioengineering*. 1998, University of Washington, Seattle, p. 15.] The bioreactor was designed such that the temperature and pH of the media could be maintained for the entire mechanical conditioning period. In addition, the bioreactor was designed such that the sample could be left in the chamber and removed from the testbed with minimal manipulation of the construct. This enabled the incubation of the sample in the same environment as the control samples with exception for the 1 hour loading period.

Briefly, the bioreactor includes four main systems; the air plenum\interface chamber, the culturing chamber, specimen attachment\transfer jig, and the load-cell interface unions.

The air plenum chamber\interface functions to provide flow of a heated air\$CO_2$ mixture to the bioreactor such that physiological condition can be maintained for cell culturing and to align the bioreactor with the existing load cell position on the biaxial testbed. The bioreactor mounts to the top of the plenum in a recessed port that has a sliding window to allow for preheating of the system prior to bioreactor installation. Ball check valves are used on the inlet and outlet of the plenum to assure that a slight positive pressure in the bioreactor is maintained for sterility. Temperature in the plenum is monitored with four AD592 integrated circuit temperature transducers (Analog Devices, Norward, Mass.) that fit into four ports (two on the inlet and two on the exhaust) in the plenum.

The culturing chamber of the bioreactor has two components, the base and midsection. The bottom of the chamber is formed by placing a semi-permeable membrane (PL732, Baxter Healthcare, Deerfield, Ill.) between the base and the midsection. This material is used to keep media within the chamber while allowing $CO_2$ diffusion and heat transfer to the media from the air flowing through the plenum.

The chamber is designed such that the test sample can be immersed in 10-15 ml of culture media. The specimen attachment/transfer jig is designed such that minimal manipulation of the test specimen would occur while installing the loading apparatus to the specimen and installing the bioreactor in the testbed. The attachment jig consists of the mounting clamps, loading rods, and holder. The mounting clamps snap onto stainless steel pins that are attached to the construct. When assembled, the construct is suspended at the zero-strain position between the clamps.

The stainless steel loading rods are the interface between the clamps and the load-cells. Attached to the load-cells are the mating dovetail slots for the loading arms. This provides an easy means for removing the bioreactor from the testbed without removing the construct from the bioreactor.

Prior to assembly and testing, all components of the bioreactor were sonically cleaned in RBS35 detergent, rinsed 3 times for 5 minutes, and UV sterilized for 30 minutes on each side. The bioreactor was assembled using aseptic techniques after which the inside of the chamber was re-sterilized with UV light for 15 minutes.

After the initial culturing period (7 days), the assembled attachment/transfer jig was carefully installed on the seeded sample and the unseeded loaded control. 10 ml or 15 ml of culture media was placed in the assembled, sterile, bioreactor, and the seeded sample was carefully transferred to the bioreactor. Samples and unseeded controls were uniaxially strained for 1 hour per day. The initial strain protocol was cyclically straining at a rate of 5 mm/min to a 10% strain on day 1, 20% strain on day 2, and 30% strain on day 3. Thereafter, the strain was maintained at 30% and 5 mm/min. However, the protocol was modified to 5% cyclic strain at 5 mm/min for two days and 10% cyclic strain at 5 mm/min for the subsequent day in an attempt to increase the testing duration.

Tissue-Engineered Construct Morphological Analysis

The day following the last successful day of straining, the specimens were prepared for analysis. Sections of the specimens were fixed in 4% paraformaldehyde (PFA) for 15 minutes, after which they were placed in PBS for later processing. Once all tests had been conducted, the PFA fixed sections were removed from the PBS, embedded in O.C.T., and flash frozen. Embedded samples were sectioned in 7 micron thick slices and stained following a standard Masson's trichrome protocol. Once the sections were stained, they were imaged with light microscopy and qualitatively analyzed for morphological features.

A portion of the PFA fixed samples from representative samples for each type of scaffold were prepared for SEM. Samples were prepared for SEM by dehydration in an alcohol gradient. Because the DPU readily dissolves in alcohol, a modified dehydration protocol was followed based on experimental analysis of the scaffold degradation time in alcohol. Samples were dehydrated in increasing alcohol concentrations from 20% to 60% in increments of 10% for three minutes in each concentration. The samples were then allowed to air dry in the laminar flow hood overnight. Once prepared, each sample was cut in half and mounted on an aluminum stud with opposite sides exposed. Samples were then sputter coated with gold for 20 seconds and SEM imaged.

Sections from representative samples for each type of scaffold used were also labeled using Qtracker™ fluorescent live cell labeling kit (QuantumDot, Hayward, Calif.) following the manufacturer's recommended protocol. Sections of the labeled samples were placed on slides and observed with fluorescent microscopy.

Tissue-Engineered Construct Biochemical Analysis Collagen Synthesis

For biochemical analysis 1.5 ml of culture media was extracted from all samples during each day of mechanical testing. Media was obtained prior to installing the attachment jig on the first day of testing, before mechanical testing for each day of testing, and the day following the termination of testing. Once the media sample was obtained, the old media was removed from the bioreactor and culture plates and fresh media was added.

The synthesis of collagen was assessed using an enzyme immunoassay kit (EIA) (PIP, Takara Miras Bio, Madison, Wis.). Collagen is synthesized as precursor molecules called procollagens. The procollagens have peptide sequences at both ends called propeptides which facilitate the winding of procollagen into the triple-helix formation. When the collagen triple-helix is secreted, the propeptides are cleaved. The kit was used to assess the quantity of propeptides synthesized which stoichiometrically represent the quantity of collagen synthesis. The sensitivity of the kit was 10 ng/ml.

Samples and standard curves were prepared following the EIA manufacturer's protocol. Once completed, the absorbance of each sample was measured at 480 nm and compared to the standard curve. Seeded samples were normalized to unseeded controls.

Results

Scaffold Properties

The two different formulations of DPU exhibited different stress-strain relationships. Stress-strain relationships of DPU appeared to be consistent between seeded and unseeded scaffolds. The DPU5050 exhibits a biphasic curve at 10% strain (Figure) and the DPU1250 exhibits a linear trend (Figure). However, the magnitude of the stress increased 100 fold with the cell seeded DPU5050, whereas the DPU1250 maintained the same maximum stress between seeded and unseeded samples.

Collagen Synthesis

Procollagen content (PCC) in the media increased with a power law relationship with respect to a decrease in the post transition modulus. The post transition modulus of the DPU5050 constructs decreased with the number of days tested, whereas the post transition modulus of the DPU1250 constructs increased with the number of days tested. Despite the difference in degradation response (decreased modulus with time verses increased modulus with time), the procollagen content was increasingly greater with a decrease in post transition modulus.

Morphological analyses were performed to qualitatively assess the biological aspects of the constructs. Masson's trichrome stain was used to assess cellular ingrowth and collagen deposition. Cellular ingrowth was observed on both scaffolds produced with DPU5050 and DPU1250. DPU5050 appeared to be more porous than fibrous, whereas DPU1250 was definitely fibrous. The greatest densities of cells were observed on DPU5050 constructs that had been mechanically loaded for 5 days after the initial 1 week of static culturing. These meshes also had more prevalent staining for collagen. Furthermore, the collagen in the samples that were loaded for 5 days was always adjacent to cellular ingrowth.

Staining for collagen revealed collagen deposition on four of nine scaffolds, all of which were produced using the DPU5050. Cells in the DPU5050 scaffolds appeared to always be confined to pores, whereas cells on the DPU1250 scaffolds could be seen growing along fibers and spreading. The DPU1250 scaffolds were loaded for up to 3 days only. Qualitatively, the seeded samples that were strained for 3 days appeared to have the greater number of cells within the mesh. Furthermore, the cellular ingrowth for the DPU1250 samples appeared to be along fibers only. There were no indications that the cells were attaching to multiple fibers within the mesh. However, the cells do appear to elongate or spread out in the direction of the fiber.

Fluorescent microspheres were used to label the live cells within the construct after which the constructs were imaged using fluorescent microscopy. The samples were fluorescent showing distinct cellular content in addition to fibrous architecture of the scaffold. At increased magnifications, the fibrous structure becomes more apparent, showing cells adhering to fibers as well as growing in interfiber spaces. As-spun and scaffolds in media did not auto-fluoresce and did not label with the fluorescent microspheres.

The constructs produced from the DPU5050 appear to have a different morphology than those produced from the DPU1250. At low magnification, there is no apparent fibrous structure; there was, however, what appears to be a substantial cellular presence on the construct. Increasing the magnification does reveal some fibrous structure and the cell migrating into the structure; however, the polymer fibers do not appear as well as the DPU1250 fibers.

Scanning electron microscopy images were used to determine if the cells were adhering to the fibers and growing within the fibroporous structure.

Laminin coated and as-spun control images were used to differentiate between scaffold features and cellular structures within the seeded scaffolds. All control images exhibit scaffolds that have smooth fibers with no debris in the interfiber spaces.

DPU5050 constructs imaged all had structures that were not present on the as-spun scaffolds. The cells appeared to be round, globular shaped and were primarily on single fibers. There were some texture regions around these structures that were most likely extracellular matrix remnants/proteins. The globular cellular structures were slightly smaller than the live cells imaged with light microscopy. In some instances, structures could be seen filling between fibers and adhering to fibers. Speculation was that these sheets were extracellular matrix proteins that had filled the voids between the fibers.

Imaging results from the DPU1250 constructs did not reveal substantial numbers of round, globular structures. However, there were several cells adhering to fibers that were spread out and extending pseudopods. In addition, there were several features that could be cells or cellular byproducts. Structures like this were not observed in the control SEM nor were structures wrapped around fibers observed in the DPU5050 constructs.

In the tissue engineering methodology used in the research, biodegradable scaffolds were seeded with cells. Thus, the mechanical properties of the scaffolds were changing with time as the scaffolds degraded. Additionally, two different formulations of DPU were used that exhibit different mechanical characteristics. However, the architectures of the scaffolds were not significantly different. The binding to these different scaffolds induced different cellular responses. The cells on the DPU5050 were balled up, whereas the cells on the DPU1250 scaffold were spread out. This response most likely resulted primarily from the elastic properties of the material. The findings indicate that the synthesis of collagen increased with a decrease in scaffold modulus. The modulus of the DPU5050 scaffolds was decreasing with time (degradation); however, the modulus of the DPU1250 scaffolds was increasing with time (strain hardening), yet they both elicited the same response with respect to collagen synthesis.

While illustrative embodiments have been illustrated and described, it will be appreciated that various changes can be made therein without departing from the spirit and scope of the invention.

The invention claimed is:

1. An electrospinning apparatus, comprising:
   (a) a reservoir configured to contain a spinning dope;
   (b) a nozzle adjacent to the reservoir through which the spinning dope is extruded or drawn;
   (c) a first electrode in contact with the nozzle;
   (d) a second electrode located a distance away from the first electrode;
   (e) a power supply connected to at least one of the first electrode and the second electrode, wherein the power supply is configured to generate an electrostatic field between the first electrode and the second electrode; and
   (f) a collection surface located between the first electrode and the second electrode, wherein the collection surface comprises a pattern of conductive material separated by dielectric material, and wherein the collection surface is isolated from the first electrode and the second electrode to interfere with, manipulate, or cause a change in the electrostatic field, wherein the conductive material is connected to a second power supply configured to generate a second electrostatic field to interfere with, manipulate, or cause a change in the electrostatic field generated between the first electrode and the second electrode.

2. The electrospinning apparatus of claim 1, wherein the collection surface comprises a plane.

3. The electrospinning apparatus of claim 1, wherein the collection surface comprises a cylindrical mandrel.

4. The electrospinning apparatus of claim 1, wherein the collection surface is configured to rotate relative to the nozzle.

5. The electrospinning apparatus of claim 1, further comprising means to control voltage generated by the power supply, the second power supply, or both the power supply and the second power supply.

6. The electrospinning apparatus of claim 1, further comprising fibers deposited on the collection surface, wherein the conductive material comprises a plurality of conductive layers aligned parallel to each other and the fibers are aligned into arrays of non-random fibers and random fibers between the arrays that attach adjacent arrays to one another.

7. The electrospinning apparatus of claim 1, further comprising a controller and a user interface configured to control a controlled parameter at a desired set point.

8. The electrospinning apparatus of claim 1, further comprising a controller and an instrument configured to have closed-loop control of at least one variable measured by the instrument.

9. The electrospinning apparatus of claim 1, further comprising means to control the temperature and/or viscosity of the spinning dope.

10. The electrospinning apparatus of claim 1, further comprising means to control the pressure of the spinning dope.

11. The electrospinning apparatus of claim 1, further comprising means to control the distance between the first electrode and the second electrode.

12. The electrospinning apparatus of claim 1, further comprising means to control the distance of the collection surface from the nozzle.

13. The electrospinning apparatus of claim 1, further comprising a controller and two or more instruments configured to have closed-loop control of two or more variables measured by the instruments.

14. An electrospinning apparatus, comprising:
   a first electrode and a second electrode between which an electrostatic field is generated; and
   a collection surface isolated from and located between the first electrode and the second electrode, wherein the collection surface comprises a pattern of conductive material separated by dielectric material, wherein the collection surface is configured to cause interference with or changes in the electrostatic field, and wherein fibers that are deposited on the collection surface are made to lie in a pattern according to the interference or changes in the electrostatic field, wherein the conductive material is connected to a power supply configured to generate a second electrostatic field to interfere with, manipulate, or cause a change in the electrostatic field generated between the first electrode and the second electrode.

15. The electrospinning apparatus of claim 14, wherein the collection surface comprises a plane.

16. The electrospinning apparatus of claim 14, wherein the collection surface comprises a cylindrical mandrel.

17. The electrospinning apparatus of claim 14, wherein the collection surface is configured to rotate relative to a nozzle through which dope is electrospun.

18. The electrospinning apparatus of claim 14, further comprising fibers deposited on the collection surface, wherein the conductive material comprises a plurality of conductive layers aligned parallel to each other and the fibers are aligned into arrays of non-random fibers and random fibers between arrays that attach adjacent arrays to one another.

19. The electrospinning apparatus of claim 14, further comprising a controller and a user interface configured to control a controlled parameter at a desired set point.

20. The electrospinning apparatus of claim 14, further comprising a controller and an instrument configured to have closed-loop control of at least one variable measured by the instrument.

21. The electrospinning apparatus of claim 14, further comprising a supply of spinning dope and means to control the temperature and/or viscosity of the spinning dope.

22. The electrospinning apparatus of claim 14, further comprising a supply of spinning dope and means to control the pressure of the spinning dope.

23. The electrospinning apparatus of claim 14, further comprising means to control the distance between the first electrode and the second electrode.

24. The electrospinning apparatus of claim 14, further comprising a nozzle through which fibers are produced and means to control the distance of the collection surface from the nozzle.

25. The electrospinning apparatus of claim 14, further comprising a power supply and means to control voltage generated by the power supply.

26. The electrospinning apparatus of claim 14, further comprising a controller and two or more instruments configured to have closed-loop control of two or more variables measured by the instruments.

* * * * *